(12) United States Patent
Swetlitz et al.

(10) Patent No.: US 11,843,920 B2
(45) Date of Patent: Dec. 12, 2023

(54) SYSTEMS AND METHODS FOR REMOTE ADMINISTRATION OF HEARING TESTS

(71) Applicant: Sonova AG, Staefa (CH)

(72) Inventors: George Swetlitz, Durham, NC (US); Brian D. Vesely, Ozark, MO (US); Martin J. Lenardon, Phoenix, AZ (US); Brian E. Owens, Manasquan, NJ (US); Matthew C. Peterse, Brick, NJ (US)

(73) Assignee: Sonova AG, Staefa (CH)

( * ) Notice: Subject to any disclaimer, the term of this patent is extended or adjusted under 35 U.S.C. 154(b) by 98 days.

(21) Appl. No.: 17/527,378

(22) Filed: Nov. 16, 2021

(65) Prior Publication Data

US 2022/0078565 A1 Mar. 10, 2022

Related U.S. Application Data

(63) Continuation of application No. 17/234,691, filed on Apr. 19, 2021, now Pat. No. 11,178,499.
(Continued)

(51) Int. Cl.
*G06F 3/0482* (2013.01)
*H04R 25/00* (2006.01)
(Continued)

(52) U.S. Cl.
CPC ............ *H04R 25/70* (2013.01); *A61B 5/123* (2013.01); *A61B 5/7475* (2013.01);
(Continued)

(58) Field of Classification Search
CPC ... A61B 1/00011; A61B 1/227; A61B 5/0022; A61B 5/12; A61B 5/121; A61B 5/123;
(Continued)

(56) References Cited

U.S. PATENT DOCUMENTS 6,322,521 B1 * 11/2001 Hou ..................... A61B 5/121
381/23.1
6,522,988 B1 * 2/2003 Hou ..................... A61B 5/121
702/108
(Continued)

FOREIGN PATENT DOCUMENTS

WO 2019028527 A1 2/2019

OTHER PUBLICATIONS

Online Hearing Test and Audiogram Printout, https://web.archive.org/web/20190127184146/https://hearingtest.online/, Apr. 19, 2020, 7 pgs.
(Continued)

*Primary Examiner* — Gerald Gauthier
(74) *Attorney, Agent, or Firm* — Greenberg Traurig, LLP

(57) ABSTRACT

A computer-implemented method includes sending, by one or more processors of one or more computing devices, first instructions to a patient electronic device causing the patient electronic device to display a first graphical user interface that facilitates a hearing test between a patient and a provider of the hearing test. The computer-implemented method further includes sending, by the one or more processors, second instructions to a provider electronic device causing the provider electronic device to display a second graphical user interface that facilitates the hearing test.

21 Claims, 47 Drawing Sheets

Related U.S. Application Data

(60) Provisional application No. 63/012,259, filed on Apr. 19, 2020.

(51) Int. Cl.
  G06F 3/16 (2006.01)
  H04N 7/14 (2006.01)
  A61B 5/12 (2006.01)
  A61B 5/00 (2006.01)

(52) U.S. Cl.
  CPC ............ G06F 3/0482 (2013.01); G06F 3/165 (2013.01); H04N 7/141 (2013.01); H04R 25/558 (2013.01); *A61B 2560/0223* (2013.01); *H04R 2225/55* (2013.01)

(58) Field of Classification Search
  CPC ..... A61B 5/125; A61B 5/1495; A61B 5/7475; A61B 2560/0223; A61B 5/0002; G06F 3/04817; G06F 3/0482; G06F 3/165; G06Q 30/02; G16H 10/20; G16H 10/60; G16H 20/30; G16H 40/67; G16H 50/20; G16H 80/00; H04N 7/141; H04R 25/30; H04R 25/55; H04R 25/70; H04R 25/558; H04R 2225/55; H04R 25/353; H04M 11/007
  See application file for complete search history.

(56) References Cited

U.S. PATENT DOCUMENTS

| | | | |
|---|---|---|---|
| 6,721,404 B1* | 4/2004 | Lashley | H04M 11/007 379/102.02 |
| 6,840,908 B2 | 1/2005 | Edwards et al. | |
| 6,916,291 B2 | 7/2005 | Givens et al. | |
| 7,016,504 B1 | 3/2006 | Shennib | |
| 7,190,795 B2* | 3/2007 | Simon | A61B 5/121 381/60 |
| 7,288,072 B2* | 10/2007 | Stott | A61B 5/12 600/559 |
| 7,450,724 B1 | 11/2008 | Greminger | |
| 7,529,545 B2 | 5/2009 | Rader et al. | |
| 7,854,704 B2* | 12/2010 | Givens | A61B 5/12 600/559 |
| 8,751,934 B2* | 6/2014 | Young | G06F 3/0482 715/727 |
| 9,326,706 B2* | 5/2016 | Shennib | A61B 5/123 |
| 10,390,155 B2 | 8/2019 | Simonides et al. | |
| 10,462,582 B2 | 10/2019 | Neumeyer et al. | |
| 10,553,196 B1 | 2/2020 | Stewart | |
| RE48,462 E | 3/2021 | Sabin et al. | |
| 11,331,008 B2* | 5/2022 | Shennib | A61B 5/123 |
| 2002/0016967 A1 | 2/2002 | Carlile | |
| 2002/0068986 A1 | 6/2002 | Mouline | |
| 2003/0078515 A1* | 4/2003 | Menzel | A61B 5/0002 600/300 |
| 2003/0083591 A1* | 5/2003 | Edwards | G16H 80/00 600/300 |
| 2005/0086058 A1 | 4/2005 | Lemelson et al. | |
| 2007/0009126 A1 | 1/2007 | Fischer | |
| 2008/0269636 A1* | 10/2008 | Burrows | A61B 5/121 600/559 |
| 2011/0026721 A1 | 2/2011 | Parker | |
| 2012/0322384 A1 | 12/2012 | Zerr et al. | |
| 2012/0324076 A1 | 12/2012 | Zerr et al. | |
| 2013/0243209 A1 | 9/2013 | Zurbruegg et al. | |
| 2013/0343583 A1* | 12/2013 | Marcoux | G16H 20/30 381/314 |
| 2014/0194774 A1* | 7/2014 | Gilligan | A61B 5/123 600/559 |
| 2014/0194775 A1 | 7/2014 | Van Hasselt et al. | |
| 2014/0243702 A1* | 8/2014 | Levine | A61B 5/123 600/559 |
| 2014/0270211 A1 | 9/2014 | Solum et al. | |
| 2014/0278450 A1* | 9/2014 | Schoenberg | G16H 10/60 705/2 |
| 2014/0309549 A1* | 10/2014 | Selig | A61B 5/123 600/559 |
| 2015/0110310 A1 | 4/2015 | Minnaar | |
| 2015/0124976 A1 | 5/2015 | Pedersen et al. | |
| 2015/0245150 A1 | 8/2015 | Jepsen et al. | |
| 2015/0257683 A1* | 9/2015 | Ashmore | A61B 5/0022 600/559 |
| 2015/0350794 A1 | 12/2015 | Pontoppidan | |
| 2016/0038062 A1* | 2/2016 | Morita | G06Q 30/02 600/559 |
| 2016/0198271 A1* | 7/2016 | Shennib | H04R 25/30 381/60 |
| 2016/0246781 A1 | 8/2016 | Cabot | |
| 2017/0180894 A1 | 6/2017 | Jepsen et al. | |
| 2017/0238106 A1 | 8/2017 | Theill | |
| 2018/0103327 A1 | 4/2018 | Mosgaard | |
| 2018/0103859 A1 | 4/2018 | Provenzano | |
| 2018/0103876 A1* | 4/2018 | Davis | G16H 80/00 |
| 2018/0109889 A1 | 4/2018 | Kang et al. | |
| 2018/0132046 A1 | 5/2018 | Westermann et al. | |
| 2018/0227682 A1* | 8/2018 | Lederman | A61B 5/123 |
| 2018/0241863 A1 | 8/2018 | Lee et al. | |
| 2018/0242090 A1 | 8/2018 | Sigwanz et al. | |
| 2018/0288541 A1 | 10/2018 | Chalupper et al. | |
| 2018/0342320 A1 | 11/2018 | Westermann et al. | |
| 2018/0350144 A1 | 12/2018 | Rathod | |
| 2018/0359573 A1 | 12/2018 | Meister et al. | |
| 2019/0132691 A1 | 5/2019 | Gehring et al. | |
| 2019/0253816 A1 | 8/2019 | Pihl et al. | |
| 2019/0274595 A1 | 9/2019 | Usher | |
| 2019/0313196 A1 | 10/2019 | Usher | |
| 2019/0356989 A1 | 11/2019 | Li et al. | |
| 2019/0364354 A1* | 11/2019 | Keady | A61B 5/123 |
| 2020/0069224 A1 | 3/2020 | Perscheid | |
| 2020/0100038 A1 | 3/2020 | Westergaard et al. | |
| 2020/0129094 A1* | 4/2020 | Levine | A61B 1/00011 |
| 2020/0152190 A1 | 5/2020 | Itkowitz et al. | |
| 2020/0178852 A1* | 6/2020 | Lardaro | A61B 5/1495 |
| 2020/0245081 A1 | 7/2020 | Elmedyb et al. | |
| 2020/0260202 A1* | 8/2020 | Cheng | A61B 1/227 |
| 2020/0345278 A1* | 11/2020 | Mortensen | A61B 5/125 |
| 2020/0413205 A1* | 12/2020 | Sheymov | H04R 25/353 |
| 2021/0243543 A1 | 8/2021 | Takahashi | |
| 2021/0258702 A1 | 8/2021 | Thiede et al. | |
| 2021/0329393 A1* | 10/2021 | Swetlitz | A61B 5/7475 |
| 2022/0078565 A1* | 3/2022 | Swetlitz | G16H 50/20 |

OTHER PUBLICATIONS

ISA/US, International Search Report and Written Opinion issued in PCT/US21/28025, dated Aug. 5, 2021, 9 pgs.

* cited by examiner

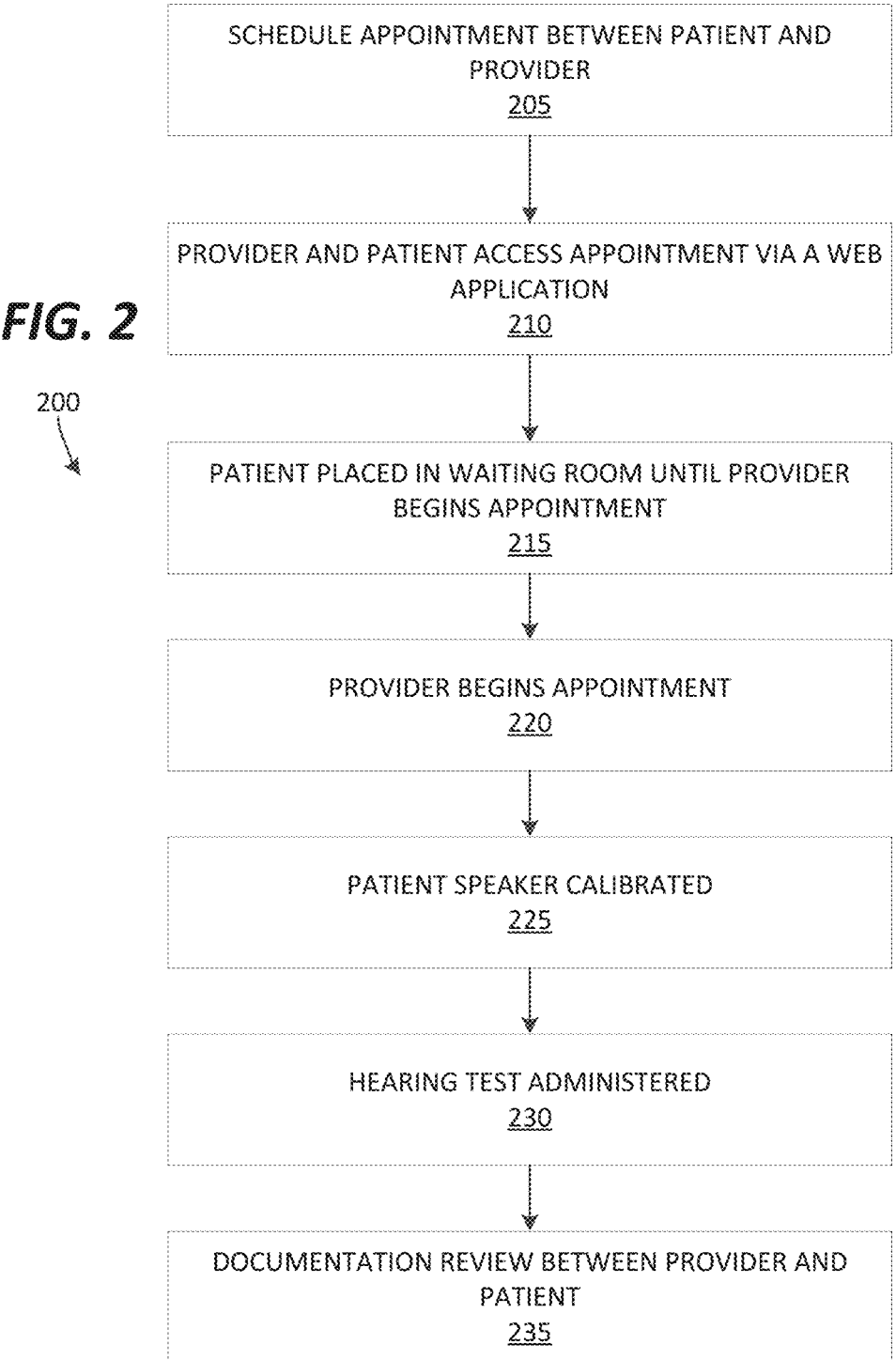

My Sessions — 300

| Provider | Patient | Scheduled Start | | |
|---|---|---|---|---|
| Provider Name 1 | Patient Name 1 | 4/15/2020 3:30 PM | Edit Session | Start Session |
| Provider Name 1 | Patient Name 2 | 4/15/2020 3:35 PM | Edit Session | Start Session |
| Provider Name 1 | Patient Name 3 | 4/16/2020 10:31 AM | Edit Session | Start Session |
| Provider Name 2 | Patient Name 4 | 4/16/2020 2:00 PM | Edit Session | Start Session |
| Provider Name 2 | Patient Name 5 | 4/16/2020 2:24 AM | Edit Session | Start Session |
| Provider Name 2 | Patient Name 6 | 4/16/2020 2:31 PM | Edit Session | Start Session |
| Provider Name 3 | Patient Name 7 | 4/16/2020 2:32 PM | Edit Session | Start Session |
| Provider Name 3 | Patient Name 8 | 4/16/2020 2:32 PM | Edit Session | Start Session |
| Provider Name 3 | Patient Name 9 | 4/17/2020 5:06 PM | Edit Session | Start Session |

Create Session — 305

310 — Provider; 315 — Patient; 320 — Scheduled Start; 330 — Edit Session; 335 — Start Session

Figure 4B:
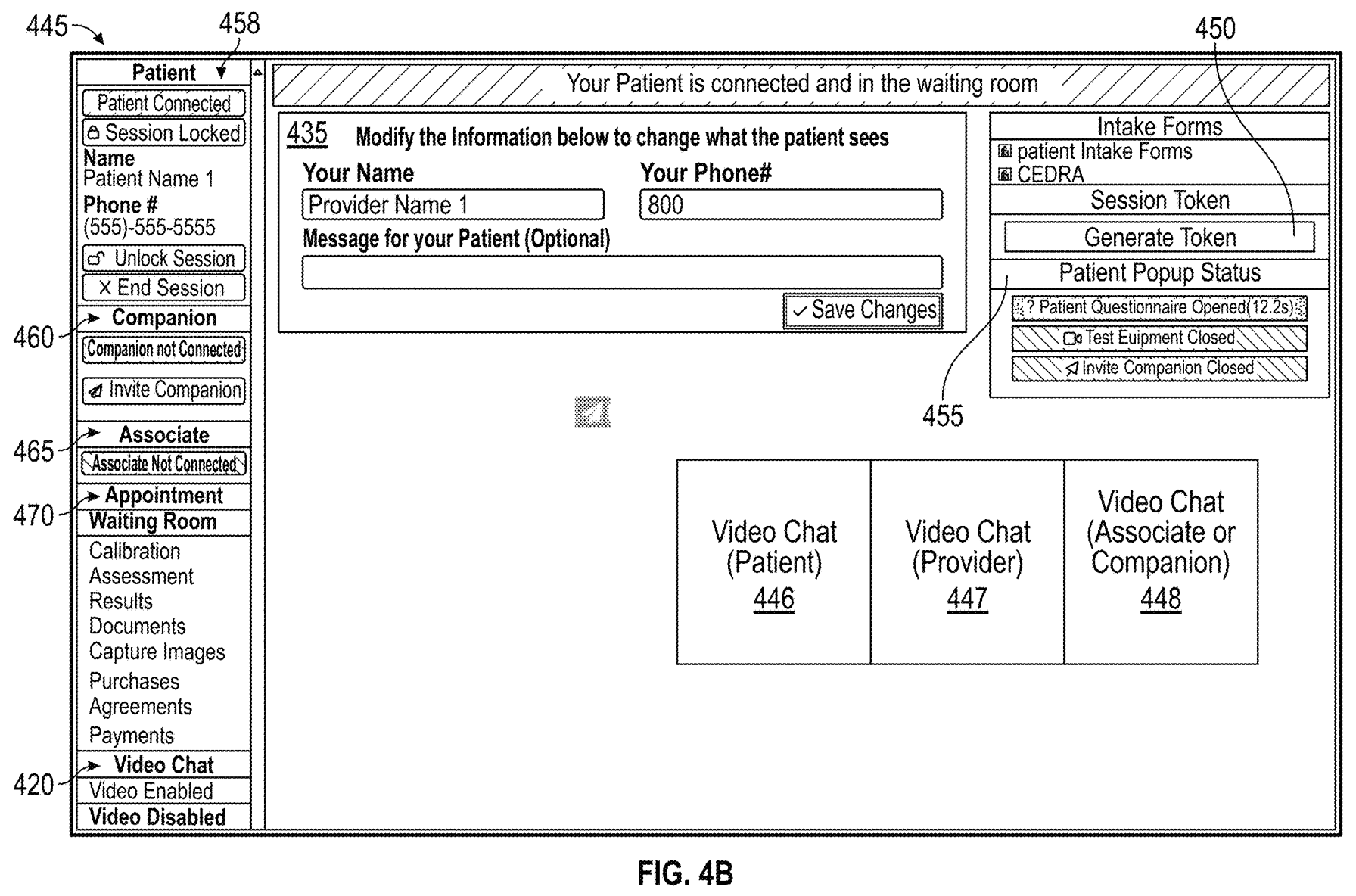

Your Patient is connected and in the waiting room

445

458 → Patient
- Patient Connected
- Session Locked
- Name: Patient Name 1
- Phone #: (555)-555-5555
- Unlock Session
- X End Session

460 → Companion
- Companion not Connected
- Invite Companion

465 → Associate
- Associate Not Connected

470 → Appointment
- Waiting Room
- Calibration
- Assessment
- Results
- Documents
- Capture Images
- Purchases
- Agreements
- Payments

420 → Video Chat
- Video Enabled
- Video Disabled

435 Modify the Information below to change what the patient sees

Your Name: Provider Name 1
Your Phone#: 800
Message for your Patient (Optional)

✓ Save Changes

450
- Intake Forms
  - patient Intake Forms
  - CEDRA
- Session Token
  - Generate Token

455 Patient Popup Status
- ? Patient Questionnaire Opened (12.2s)
- ☐ Test Equipment Closed
- ✓ Invite Companion Closed Video Chat (Patient) 446

Video Chat (Provider) 447

Video Chat (Associate or Companion) 448

475 ↴

Intake Forms

📊 Patient Intake Form

📊 CEDRA

450

Session Token

[ Generate Token ]

455

Patient Popup Status

▨▨▨ ? Patient Questionaire Closed (35.1s) ▨▨▨

░░░ 🎥 Test Equipment Opened ░░░

▨▨▨ ➤ Invite Companion Closed ▨▨▨

Intake Forms

📊 Patient Intake Form

📊 CEDRA

Session Token

485
2xaYeN ←

455

Patient Popup Status

▨▨▨ ? Patient Questionaire Closed (35.1s) ▨▨▨

▨▨▨ ☐ Test Equipment Opened ▨▨▨

▨▨▨ ➤ Invite Companion Closed ▨▨▨

FIG. 4D

Intake Questionnaire

First Name
Patient

Last Name
Name 1

Birth Dtae
mm/dd/yyyy

Address
123 Main St

City
Anywhere

State
NJ

Zip
99999

Home Phone
(999)999-9999

Mobile Phone
(555)555-5555

Email
Patientname1@email.com

Sex
◉ Male ○ Female

Employment Status
◉ Employed ○ Retired ○ Other

Marital Status
○ Married ◉ Single ○ Other

Referred by

How did you hear about us?
Have you had your hearing tested? ○ Yes ○ No
Do you currently wear hearing aids? ○ Yes ○ No
Have you been having trouble recently? ○ Yes ○ No
Who suggested you have a hearing test?

⇨ Next  ✓ Save & Close

FIG. 5C

Questions about your Hearing Health

Select "Yes" or "No"

1. When talking on a telephone, do you understand what people say better in one ear than the other? [Yes] [No]
2. Did the hearing loss in either of your ears develop suddenly? [Yes] [No]
3. Have you ever had a sudden permanent change in your hearing? [Yes] [No]
4. Do you have hearing loss in only one ear? [Yes] [No]
5. Do you hear better in one ear than the other? [Yes] [No]
6. Does your hearing change from day to day? [Yes] [No]
7. As an adult, have you ever had more than one infection in the same ear during one year? [Yes] [No]
8. Have you ever noticed pus, blood or other active fluid discharged from your ear? [Yes] [No]
9. Have you ever been told by a physician that you have Meniere's [Yes] [No]

⇒Next  ✓Save&Close

FIG. 5D

Waiting Room   Calibration   Assessment   Results   Documents   Purchases   Agreements   Payments Provider Name 1   Companion Name   Patient Name 1

SoundBenefits     1405

The results are in!
Your HearScore is 5.

With this score, you may:
- Have to ask people to speak a little louder or repeat themselves
- Notice more difficulty understanding speech when there is background noise
- Respond inappropriately or not know when someone is talking to you
- Be able to hear speech but have difficulty understanding the words
- Hear from your kids and/or spouse that they think you have a hearing problem
- Have tinnitus (ringing in the ears)

5/10   10 being the best

What does this mean?
With a HearScore of 5, you are already missing out on things. Early intervention is always best practice when it comes to your hearing. The sooner you treat your hearing loss:

When you're in a noisy environment, your HearScore will likely drop to: 1
Understanding speech clearly in background noise can be difficult for anyone. When you have untreated hearing loss, it becomes significantly more difficult.

You can contact your provider by phone at 555-555-5555

| Patient | | | | | | |
|---|---|---|---|---|---|---|
| ☐ Patient Connected | Category | Manufacturer | | Item | Select Ear | |
| ⊜ Session Locked | Hearing Aid ▽ | Select... ▽ | | Select... ▽ | Left | Right |
| Name | Gain | Receiver Length | Color | Dome & Sleeve | | |
| Patient Name 1 | Select... ▽ | Select... ▽ | Select... ▽ | Select... ▽ | | |
| Phone # | List Price | Discount | | Amount | | |
| (555)555-5555 | 0 | 0 | | 0 | | |
| ⟲ Unlock Session | | | | 2015 ✕ Cancel ✓ Save | | |
| ✕ End Session | | | | | | |
| Companion | | | | ⦿ Display to Patient | | |
| ☑ Companion Connected | | | | | | |
| Companion Name | Ear Model | | List Price | Discount | Amount | |
| ⊗ Remove Companion | Right Hearing Aid Type A | | $1,000 | ($0) | $1,000 | ☑ ☐ |
| Associate | Gain:M/60 Receiver Length:2 Color: Beige Dome: 6mm Closed | | | | | |
| Associate Not Connected | Left Hearing Aid Type B | | $1,000 | ($0) | $1,000 | ☑ ☐ |
| Appointment | Gain:M/60 Receiver Length:2 Color: Beige Dome: 6mm Closed | | | | | |
| Waiting Room | | | | Sales Tax: | 0 | |
| Calibration | | | | | | |
| Assessment | | | | Total: | $2,000 | |
| Results | | | | | | |
| Documents | | | | | | |
| Capture Images | | | | | | |
| Purchases | | | | | | |
| Agreements | | | | | | |
| Payments | | | | | | |
| Video Chat | | | | | | |
| Video Enabled | | | | | | |
| Video Disabled | | | | | | |

| Patient | | |
|---|---|---|
| Patient Connected | Remaining Amount: $2,000 | |
| 🔒 Session Locked | | |
| Name | Purchases 2105 | |
| Patient Name 1 | Hearing Aid Type A | $1,000 |
| Phone # | Hearing Aid Type B | $1,000 |
| (555)555-5555 | Purchase Total: | $2,000 |
| ⟲ Unlock Session | Sales Tax: | $0 |
| ✕ End Session | Total: | $2,000 |
| Companion | Pay Now: | 2,000 |
| Companion Connected | Remaining: | $0 |
| Companion Name | ○ Send to Patient — 2115 | |
| ⊗ Remove Companion | ○ Send to Companion | |
| Associate | 2110 | 2120 |
| Associate Not Connected | | |
| Appointment | | |
| Waiting Room | | |
| Calibration | | |
| Assessment | | |
| Results | | |
| Documents | | |
| Capture Images | | |
| Purchases | | |
| Agreements | | |
| Payments | | |
| Video Chat | | |
| Video Enabled | | |
| Video Disabled | | |

Transaction completed successfully with Confirmation number 4005836007

Total Paid Amount: $2,000

Purchases — 2205

| | |
|---|---|
| Hearing Aid Type A | $1,000 |
| Hearing Aid Type B | $1,000 |
| Purchase Total: | $2,000 |
| Sales Tax: | $0 |
| Total: | $2,000 |

Transactions — 2210

| | |
|---|---|
| Payment 1 (patient Via cc): | ✓ $2,000 |
| Total Paid Amount | $2,000 |
| Pay Now: | 0 |
| Remaining: | $0 |

2215

2000

Patient
- Patient Connected
- Session Locked

Name
Patient Name 1

Phone #
(555)555-5555
- Unlock Session
- X End Session

Companion
- Companion Connected
- Companion Name
- Remove Companion

Associate
- Associate Not Connected

Appointment
- Waiting Room
- Calibration
- Assessment
- Results
- Documents
- Capture Images
- Purchases
- Agreements
- Payments

Video Chat
- Video Enabled
- Video Disabled

SYSTEMS AND METHODS FOR REMOTE ADMINISTRATION OF HEARING TESTS

CROSS REFERENCE TO RELATED APPLICATION

This application is a continuation of and claims priority to U.S. patent application Ser. No. 17/234,691, filed on Apr. 19, 2021 (now granted as U.S. Pat. No. 11,178,499), which claims priority to and the benefit of U.S. Provisional Appln. No. 63/012,259, filed on Apr. 19, 2020, the disclosure of each if which are incorporated herein by reference in their entireties.

BACKGROUND

Hearing tests are commonly used to determine and diagnose different types of hearing loss or other ear-related medical conditions. Some hearing tests are used to determine the type and/or degree of hearing loss, and the results of such tests may be used to treat a patient with hearing loss. In some instances, the results of such a test may be used to configure hearing aids for the user based on the specifics of their hearing loss.

SUMMARY

An illustrative computer-implemented method includes sending, by one or more processors of one or more computing devices, first instructions to a patient electronic device causing the patient electronic device to display a first graphical user interface that facilitates a hearing test between a patient and a provider of the hearing test. The computer-implemented method further includes sending, by the one or more processors, second instructions to a provider electronic device causing the provider electronic device to display a second graphical user interface that facilitates the hearing test.

BRIEF DESCRIPTION OF THE DRAWINGS

FIG. 2 is a flow chart illustrating an example method for remotely administering hearing tests, in embodiments.

FIG. 3 is an example graphical user interface (GUI) for displaying scheduled appointments on a provider device, in embodiments.

FIGS. 4A-4B are example GUIs for setting a waiting room message for a patient on a provider device, in embodiments.

FIGS. 4C and 4D are example GUIs for generating a secure session token and displaying patient popup window status on a provider device, in embodiments.

FIGS. 5A-5E are example GUIs of a waiting room for a patient on a patient device, in embodiments.

FIG. 14 is an example GUI for displaying documentation on a patient device, in embodiments.

FIG. 16 is an example GUI for entering purchase information on a patient device, in embodiments.

FIG. 20 is an example GUI for entering and displaying purchase information on a provider device, in embodiments.

FIG. 21 is an example GUI for sending purchase information to a patient and/or guest device, in embodiments.

FIG. 22 is an example GUI for displaying purchase confirmation information on a provider device, in embodiments.

FIG. 25 is an example GUI for displaying documentation on a guest device, in embodiments.

FIG. 27 is an example GUI for managing hearing test appointments on a provider device, in embodiments.

DETAILED DESCRIPTION

Hearing tests are often performed for persons who have experienced hearing loss. For example, a pure tone hearing test is often administered to patients who have potentially experienced hearing loss. During such a test, different frequency sounds are played at different volume/loudness levels, and the quietest sounds the patient can hear at each frequency for each ear is noted in an audiogram. The audiogram therefore synthesizes information about the patient's ability to hear, and can be used to treat the patient for their hearing loss. In some examples, the audiogram is used to customize a hearing aid so that the hearing aid for the patient is tailored specifically to a patient's particular hearing loss, including specifics of the frequency and loudness that the patient has difficulty hearing in each ear.

Many factors can affect proper administration of a hearing test, as patients must listen for a sound and indicate to a provider administering the test whether they have heard the sound or not. Thus, noise in the environment, the speaker on which the sounds are played, and the effectiveness of communication between the patient and provider can all affect the accuracy of the results of the test.

Described herein are various systems, methods, and computer readable media for remotely administering hearing tests. For example, a provider and patient may be in separate, physically remote locations on respective electronic device connected through the internet. A live communication may be established between the provider and patient devices so that the provider and patient may communicate and a hearing test may be properly administered.

Figure 1A:
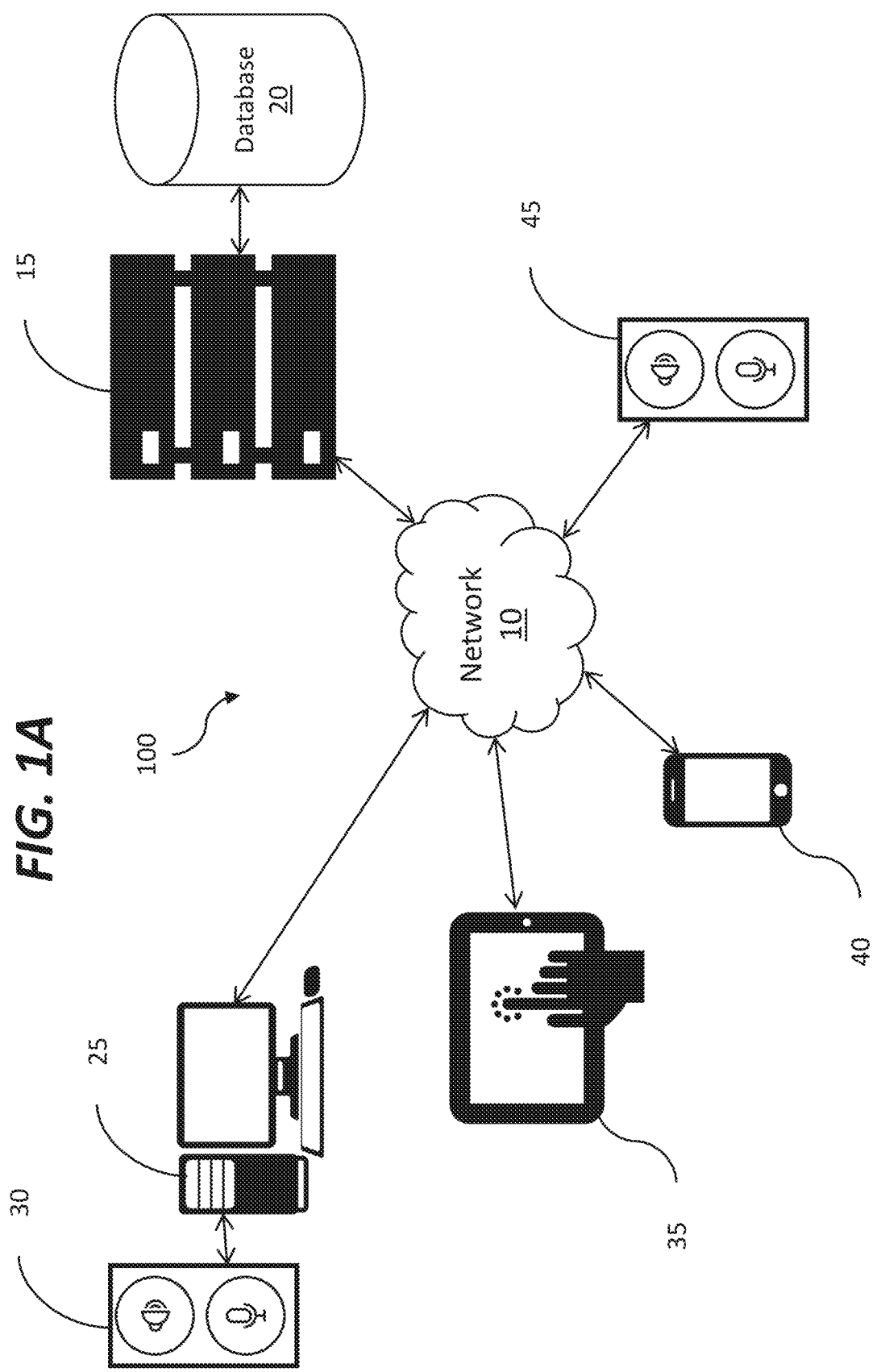
FIGS. 1A and 1B are block diagrams of example systems for remotely administering hearing tests, in embodiments.
Figure 1B:
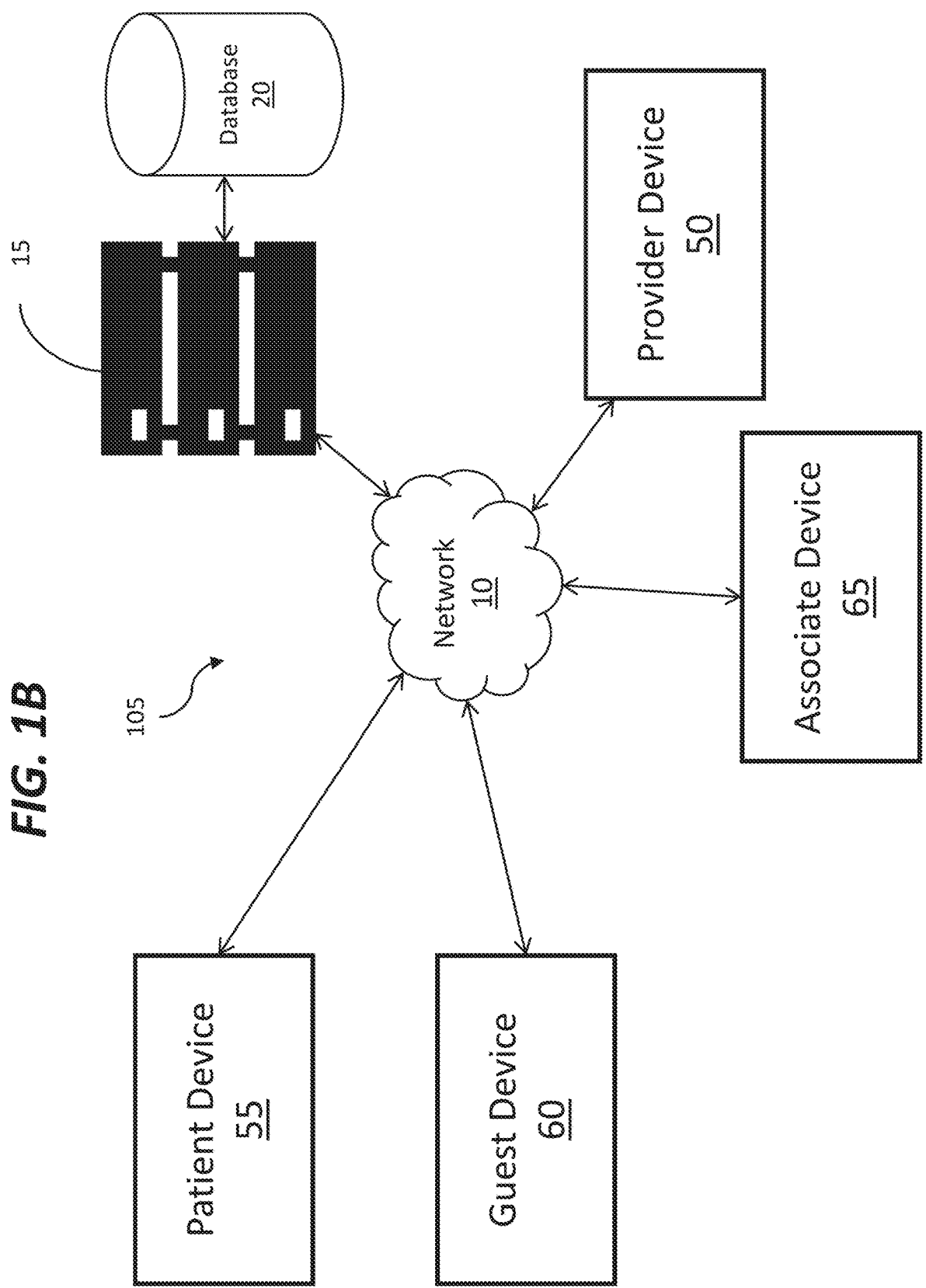

First, with respect to FIGS. 1A and 1B, illustrative systems for remotely administering a hearing test will be described at a high level. With respect to FIG. 2, an illustrative method of administering a hearing test will be described at a high level. With respect to FIGS. 3, 4A-4D, 6A-6C, 8A, 8B, 9, 10, 12A-12D, 19-22, and 27, example graphical user interfaces (GUIs) for display on a provider device during administration of a hearing test will be described. With respect to FIGS. 5A-5E, 7A, 7B 11A, 11B, 13A-13D, and 14-18, example graphical user interfaces (GUIs) for display on a patient device during administration of a hearing test will be described. With respect to FIGS. 23-26, example graphical user interfaces (GUIs) for display on a guest device during administration of a hearing test will be described. Finally, with respect to FIG. 28, an illustrative computing environment that may be used in conjunction with the methods and processes of this disclosure will be described.

Referring to FIG. 1A, a system 100 for communication between example electronic devices is shown. A server 15 is in communication with a database 20, and may communicate with other devices through a network 10. The network 10 may include internet infrastructure, may be local network, or may include any other network components that facilitate communication between electronic devices. A desktop computer 25, tablet 35, smart phone 40, and digital assistant 45 (e.g., Amazon Alexa™, Google Home™, etc.) may all communicate with one another and/or the server 15 via the network 10. The desktop computer 25 may also communicate with a speaker/microphone device 30. The other devices (e.g., tablet 35, smart phone 40, personal assistant 45) may have a speaker and microphone built in. Any other type of electronic device and/or configuration of speakers and microphones (e.g., headphones) may be used in various embodiments in administration of a hearing test. In the various embodiments described herein, a provider, a patient, and/or a guest may use any of the types of devices shown in FIG. 1 to communicate, including with voice communication, video, and/or through a GUI. A GUI may be displayed on any of the computing devices, for example through a web browser, application, or any other method for displaying GUIs on a computing device. In an example where the digital assistant 45 is used, the digital assistant 45 may play and/or receive audio for the video call between the provider and the patient, and the GUI may be displayed to patient and/or provider on a different device (e.g., desktop computer 25, tablet 35, smart phone 40).

FIG. 1B illustrates a system 105 for communication between a patient device 55, a provider device 50, and the server 15. The server 15 may facilitate the communication between the patient device 55 and the provider device 50. In addition, the server may facilitate communication between the patient device 55 and/or the provider device 50 with a guest device 60 and/or an associate device 65. Any of the devices 50, 55, 60, and 65 may be any type of or any combination of the devices shown in and described with respect to FIG. 1A. A guest may be, for example, a family member of the patient, and may hear audio from the patient device 55 and/or provider device 50, as well as may view video from the patient device 55 and/or provider device 50. In various embodiments, the guest device 60 may also have a GUI on which a display similar to what is displayed for the patient device 55 is send from the server 15 to the guest device 60. In this way, the guest device 60 may be able to see the same thing the patient device 55 does, so that a family member or other guest may assist the patient and/or provider in administering a hearing test. In various embodiments, while the guest device 60 may see the same GUI as the patient device 55, the GUI may not be interacted with by the guest. For example, when a patient is directed to indicate when they hear a sound during a hearing test by interacting with a user interface element (e.g., button), the user interface element may be displayed on a GUI of both the patient device 55 and the guest device 60, but the guest device version of the GUI does not allow the guest to click the button or otherwise indicate they have heard they sound since they are not the subject of the hearing test. While only one guest device 60 is shown in the example of FIG. 1B, multiple guest devices may also be part of a session, be able to hear audio from the provider and the patient, and/or see the video of the provider. In various embodiments, one or more guest devices may also be able to see video of the patient.

The associate device 65 may be a device of a person affiliated with the provider, such as an assistant, payment processor, hearing aid technician, or any other person that may assist a provider in administration of a hearing test, selling of a hearing aid device, etc. As such, the associate device 65 may communicate with any of the server 15, the patient device 55, the guest device 60, and/or the provider device 50.

During a hearing test, as described further herein, the server 15 may facilitate real-time audio and/or video communications between the devices 50, 55, 60, and 65. This may be accomplished, for example, through a web application that is hosted by a web application server such as the server 15. The web application may be accessed, for example, through web browsers of the devices 50, 55, 60, and 65. In various embodiments, other methods may be used, such as a particular application (app) that is installed on one or more of the devices 50, 55, 60, and 65 for implementing the systems, methods, and GUIs described herein.

Referring to FIG. 2, a method 200 for remotely administering a hearing test is described. As the various operations of FIG. 2 are described, the GUIs of FIGS. 3-27 will also be described, as FIGS. 3-27 illustrate example GUIs that may be displayed on example patient, provider, and/or guest devices as described herein.

In an operation 205 of the method 200, an appointment or session between a patient and a provider may be scheduled. FIG. 3 shows a GUI 300 that may be displayed on a provider device for scheduling an appointment/session. The GUI 300 includes a create session button 305. The button 305 may be selected to create or schedule an appointment or hearing test with a patient. Example sessions that have already been scheduled are shown in the GUI 300. Each example session includes a provider name 310, patient name 315, and scheduled time 320. In addition, each already scheduled session has an edit session button 330 and a start session button 335. The button 330 allows the provider to change the details of the session, and the button 335 allows the provider to start the session (e.g., move to the waiting room shown in FIG. 4A or 4B for the provider and FIG. 5A or 5B for the patient).

In an operation 210 of FIG. 2, the provider and the patient access the appointment via a web application. The web application may be accessed by entering a URL into a web browser, by selecting a link provided via an email, text message, etc., or by any other methods. For example, after an appointment is scheduled, the server may automatically send an email to the patient with a link for accessing the web application. After selection of such a link, the patient device may open a web browser and be navigated to the web application (e.g., the waiting room GUI 500 of FIG. 5A or GUI 515 of FIG. 5B, discussed further below). In various embodiments, a provider that is viewing the GUI 300 of FIG. 3 may have already accessed the web application through which the hearing test is hosted, so they do not need to separately access the web application after scheduling the appointment. For example, a provider may access start the appointment by selecting the button 335 of GUI 300.

Figure 4A:
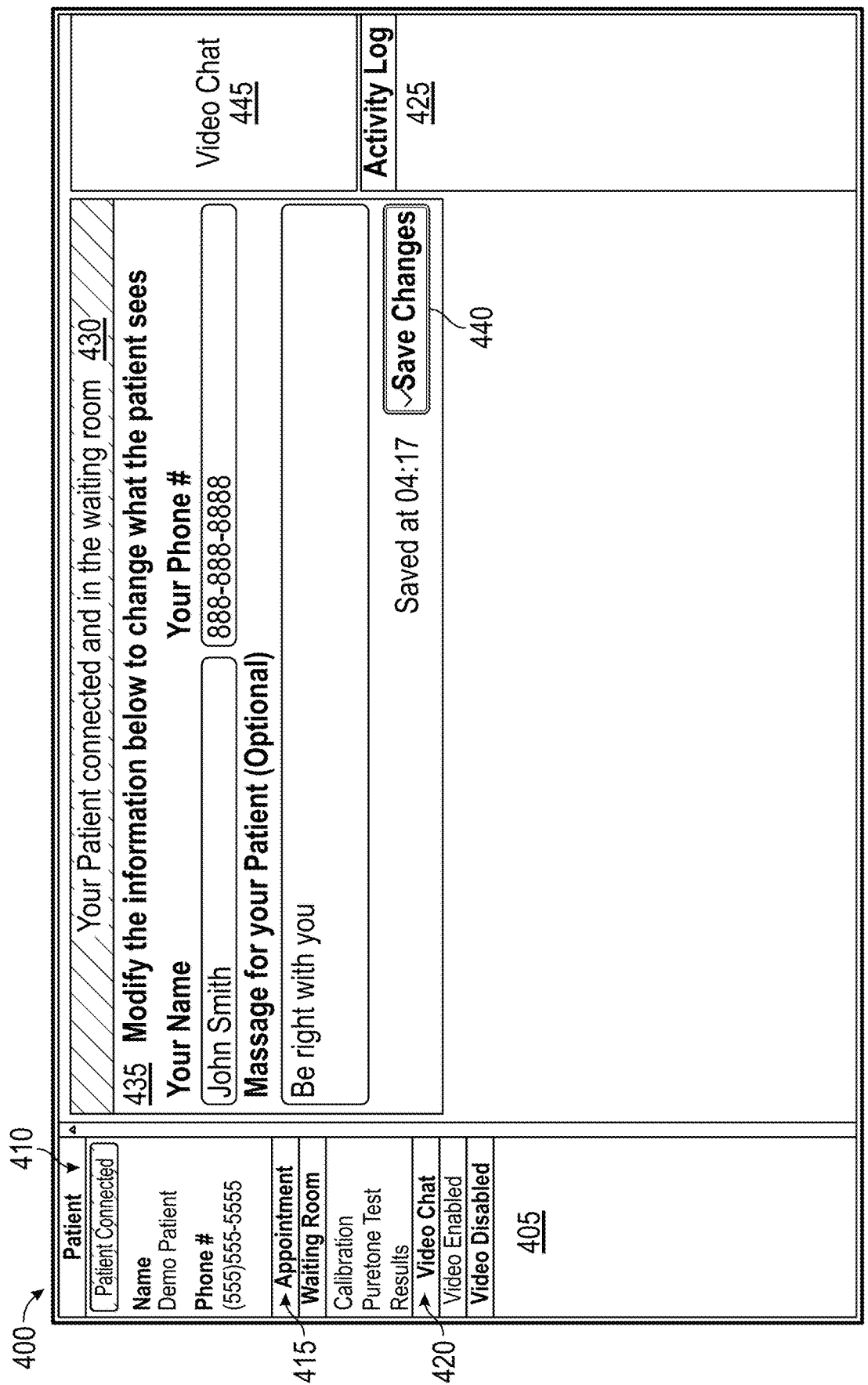

At an operation 215 of FIG. 2, the patient is placed in a waiting room until the provider begins an appointment. A GUI 500 of FIG. 5A or GUI 515 of FIG. 5B show example virtual waiting rooms a patient may see while waiting for an appointment to start. GUIs 400 and 445 of FIGS. 4A and 4B show examples of what a provider device may display after the button 335 of the GUI 300 is selected.

On the GUI 400, a status indicator 430 may indicate whether the patient device has properly accessed the appointment and launched the web application. The status indicator may indicate using color and/or text that the patient is ready and waiting for the appointment (e.g., the background may be red when the patient has not accessed the appointment yet and may be green when the patient has accessed the appointment). A patient dialog 410 may include further information about the patient, including their name, phone number, and whether the patient is currently connected to the web application.

The GUI 400 further includes an appointment tab 415. The tab 415 includes selectable elements that, when selected by the provider, navigate the provider and the patient through the appointment. Selecting the different elements in the tab 415 may cause the GUI on the patient device and/or the provider device to change when a new phase of the appointment is selected. Currently selected in the tab 415 of the GUI 400 is the waiting room. The dialog 435 further allows the provider to provide information to the patient in the waiting room. For example, the provider name, phone number, and/or a custom message may be input into the dialog 435 and saved using a button 440. When the information is saved, it may be sent to the patient device for display, for example on the GUI 500 of FIG. 5A or the GUI 515 of FIG. 5B.

The GUI 400 further includes a video chat 445 and an activity log 425. The activity log 425 is empty in the GUI 400 because the appointment has not yet begun. While the activity log 425 is currently empty in the GUI 400, the activity log 425 may, in various embodiments, show that a patient has joined the appointment, is waiting in the waiting room, and the time the patient joined. The video chat 445 may show video of the patient once the appointment begins if the video chat is toggled on in tab 420 of the GUI 400.

FIG. 4B shows another example of a GUI that may be displayed on a provider device before a hearing test begins. The GUI 445 may specifically include the dialog 435 for setting a message and other information that may be displayed on the patient device for the patient to see. The GUI may also include a patient tab 458 that indicates whether or not the patient is connected to the session or not. The patient tab 458 further includes buttons for unlocking or ending a session. The end session button may terminate a session between the provider and patient, and disconnect the patient device (and any guest device) from the session. A guest or guest device may be referred to herein as a companion or companion device, respectively.

In various embodiments, the session may be only joinable a single time by a patient device. This may occur for security purposes, to prevent unauthorized parties from accessing the session using a join link, for example. Once the patient joins, the session may be locked so that no one else may join (except for a designated guest or companion that may join using a separate invite/link than the one the patient joined with). However, if the guest or patient becomes disconnected during the session, the provider may unlock the session using the unlock session button in the patient tab 458 so that the guest or patient may rejoin the session. In various embodiments, a new security token may also be generated and used to authorize the patient rejoining the session. The provider may cause a new security token to be generated using the generate token button 450, which may cause a token to be sent to the patient or guest's device. In some embodiments, the token may be additionally or alternatively be displayed on the provider's device, and the provider could relay the token to the guest or patient over the phone, for example, so that the token could be used to rejoin the session. When the token is generated based on the provider selecting the generate token button 450, the token may be displayed as token 485 as shown in GUI 480 of FIG. 4D. As such, the security token may further enhance security for situations where the guest or patient may need to reconnect to a session. In various embodiments, a security token may also be used for patients or guests that may not otherwise have access to a secure invitation link to a remote hearing test. For example, a patient using a shared computer in a library or nursing home or other group setting may have access to the internet and may not have access to their own email account. However, using the secure token, the patient may receive the token (e.g., verbally over the phone in a conversation with the provider) and enter the token on the patient device (e.g., at a website) to enter the hearing test. In this way, individuals may receive and access a remote hearing test without needing to receive a secure link to join the hearing test.

Figure 23:
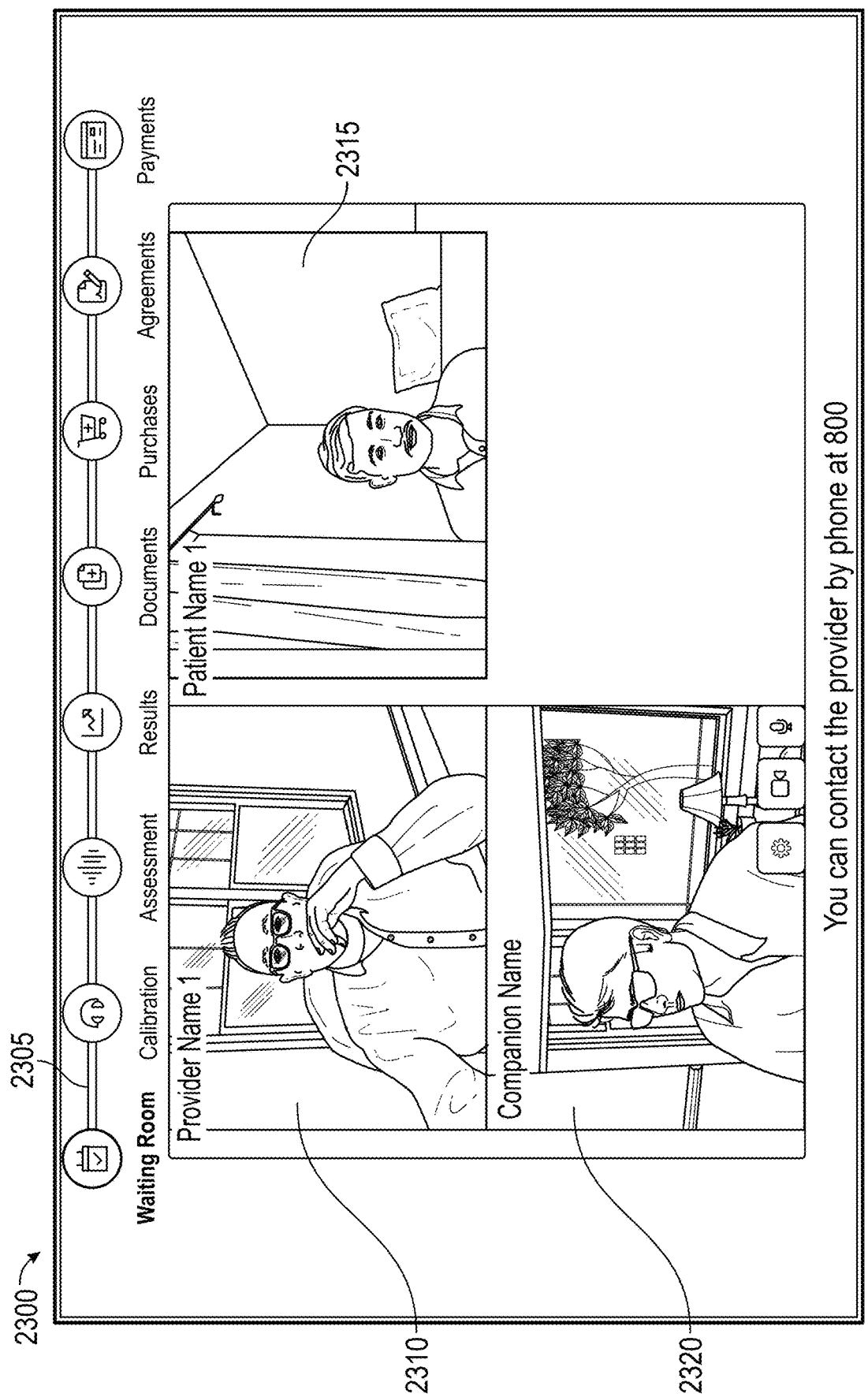
FIG. 23 is an example GUI for a waiting room for a guest device, in embodiments.

A companion tab 460 may indicate a status of a companion. In the example of FIG. 4B, a companion or guest device is not connected. However, the companion tab 460 may include an invite companion button, so that the provider may assist the patient in inviting a companion or guest for the session if desired. Once a companion has joined and is in a companion waiting room (e.g., as shown in FIG. 23), the companion tab 460 may indicate that the companion or guest has joined the session. Similar to the appointment tab 415 of FIG. 4A, an appointment tab 470 of FIG. 4B may show where in the session the devices currently are, and may be used to navigate to a new part of the session by selecting one of the options in the appointment tab 470 (e.g., the calibration portion of the session). When a companion or guest attempts to join, the provider and/or the patient may be prompted to allow the companion or guest to join. This may enhance security of the hearing test and a patient's confidential medical records. In various embodiments, a companion or guest (or anyone else) may also be prevented from joining a session while a hearing test portion of the session is underway. In this way, security may be enhanced by preventing people from joining during a hearing test and interfering with the hearing test in some way. In addition, such a system may prevent interruption of the hearing test to help ensure the test is accurate and that the patient does not get distracted or misses a tone they may have otherwise heard.

An associate tab 465 may also indicate whether an associate has joined a session. An associate may be related to a provider or part of the same entity or clinic as the provider. The associate may assist with administrative tasks related to a hearing test, such as getting the patient ready for the hearing test, make purchases after a hearing test, or any other function not related to the hearing test itself. Accordingly, the associate may join to assist the provider in certain aspects described herein that are not strictly related to the hearing test to lessen the burden on a provider of the administration of the hearing test itself. As such, an associate may see GUIs similar to that of the provider device GUIs described herein, and also may have a video chat established with a provider device, a patient device, and/or a guest/companion device. In various embodiments, a provider may hand off control of the hearing test or other portion of a session and vice versa. The associate may also control or participate in the hearing test portion of the session if they are qualified to do so.

A patient popup status tab 455 further shows how and whether the patient may be using and/or completing various features and/or popups available to the patient while the patient is in a waiting room (e.g., at the GUI 515 of FIG. 5B). The patient may access, for example, a questionnaire, video/audio testing, and/or an invite companion feature while in a waiting room such as that shown in FIG. 5B. The information in the tab 455 may indicate whether the patient has used those features, and whether their use of those features is complete (e.g., whether the patient has answered all questions in a questionnaire, whether a companion or guest invite has been successfully sent, whether audio/video equipment has been tested and is working). For example, in the GUI 445 of FIG. 4B, the tab 455 indicates that a patient questionnaire is open and has been in use for 12.2 seconds, while also indicating that the test equipment and invite companion has not yet been opened or used. In FIG. 4C, the GUI 475 shows that the test equipment is currently opened and in use. While the test equipment indicator in the tab 455 indicates whether the test equipment dialog is open or not, in other embodiments the tab 455 may additionally or alternatively indicate whether something is completed as well as whether the dialog is open or closed. In the GUI 480, all three dialogs are indicated as being closed in the tab 455.

Figure 5A:
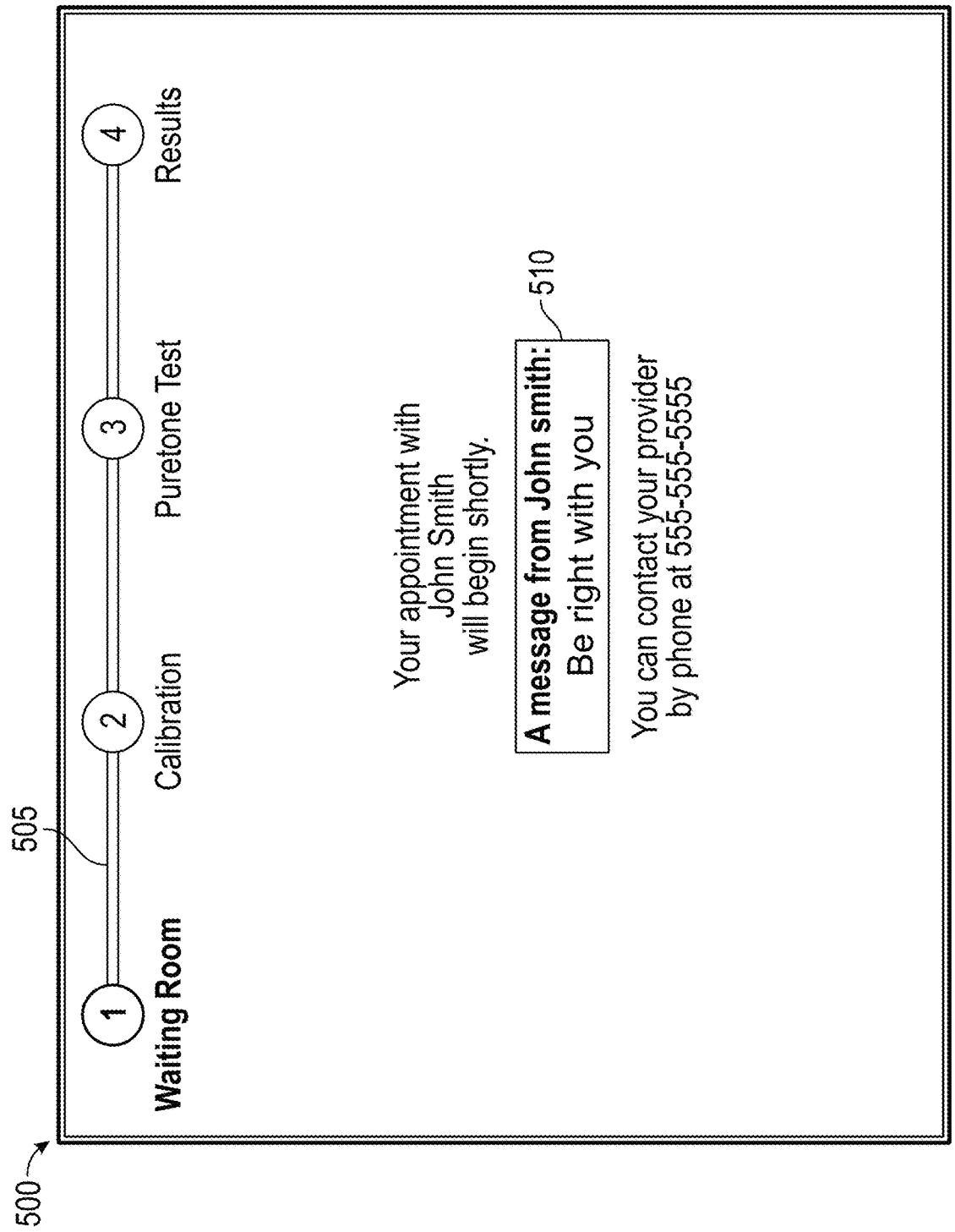
Figure 5B:
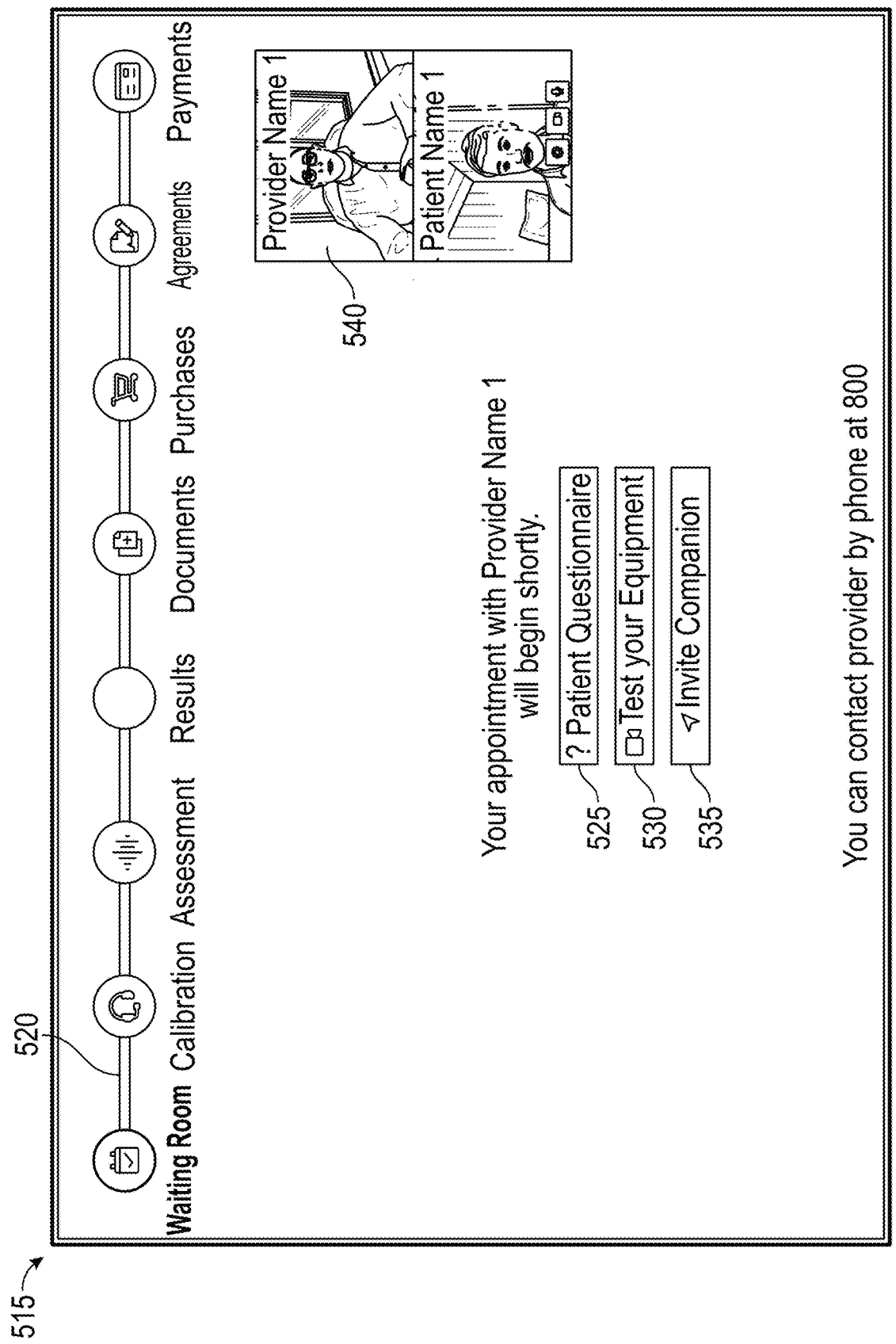
Figure 5E:
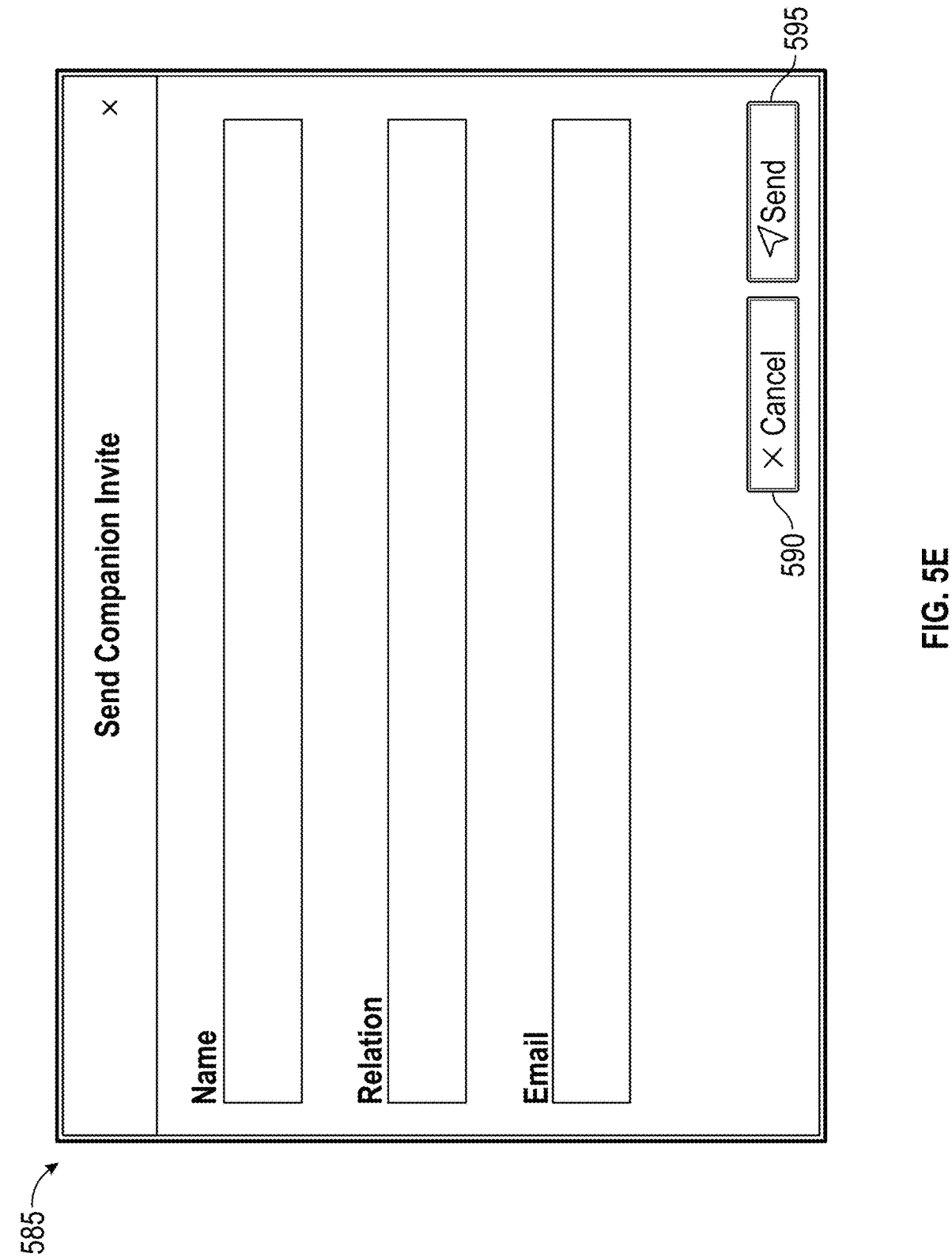

The GUI 500 of FIG. 5A and GUI 515 of FIG. 5B show example waiting rooms that the patient device may display before an appointment is started. For example, a message 510 as input by a provider through the GUI 400 of FIG. 4A is displayed in the waiting room. An appointment progress status 505 is also displayed on the GUI 500. For example, the circled one (1) of the GUI 500 is displayed red to show the patient they are currently in the waiting room, waiting for their appointment to being. In the example of FIG. 5B, the GUI 515 includes a progress status 520, a video chat 540 showing video of a patient and provider, and buttons 525, 530, and 535. The buttons 525, 530, and 535 may access a patient questionnaire, video/audio testing features, and/or invite companion features. These buttons may access further dialogs or pop ups, and the indictors in the tab 455 of FIGS. 4B-4D may indicate a status of those popups as used by the patient.

GUI 550 of FIG. 5C shows an example patient questionnaire that may be accessed by selecting the button 525. Additional portions of a patient questionnaire may be access by selecting a button 555, or the additional pop up tabs related to the buttons 530 and/or 535 may be accessed by selecting the button 555. The patient questionnaire may also be saved and closed by selecting a button 560. GUI 570 of FIG. 5D shows an additional screen of a patient questionnaire that may be accessed after the patient selects the button 555, for example. GUI 585 of FIG. 5E includes a dialog for a patient to invite a companion or guest. The invitation may be sent using a button 595, or a patient may exit the GUI 585 by selecting a button 590.

At an operation 220 of the method 200, the provider begins the appointment. For example, the provider may do so by selecting calibration in the tab 415 of the GUI 400 or in the tab 470 of the GUI 445. After the provider selects calibration in the tab 415 of the GUI 400 or in the tab 470 of the GUI 445 to begin the appointment, the provider device may display the GUI 600 of FIG. 6A or the GUI 630 of FIG. 6B for calibrating audio for the hearing test. Similarly, after the provider selects calibration in the tab 415 of the GUI 400 or in the tab 470 of the GUI 445 to begin the appointment, the patient device may display the GUI 700 of FIG. 7 or GUI 750 of FIG. 7B for calibrating audio for the hearing test.

The GUI 600 shows a calibration audio dialog box 605 for the provider. Buttons 610 allow the provider to select left ear, stereo (e.g., both ears), or right ear for outputting a calibration audio to a speaker associated with the patient device. A button 615 allows the provider to start or stop the calibration audio on the patient device. In other words, the provider device can control when audio is played on the patient device. The buttons 610 allow for the calibration audio to be played through a right side (right ear) speaker, a left side (left ear) speaker, or both. This may be helpful, for example, to ensure that a patient has headphones on the correct ear, or otherwise has their speakers configured correctly so each ear can be properly checked. If this is not checked, hearing test results may be recorded for the wrong ear, resulting in configuration of hearing aids that is not correct.

An indicator 620 indicate that audio is actually being output by a browser of the patient device or otherwise being played by the patient device. For example, in a web application hosted by a web server, the web application running on the browser of a patient device may identify when audio is being output by the web application on the patient device and send that status to the web application server and/or the provider device. While that audio is being indicated as playing, the indicator 620 may indicate so by changing color and/or text within the indicator 620. This allows the provider to see exactly when the audio is playing so the provider can ensure that the reaction of the patient is actually to audio being controlled by the provider.

Figure 6A:
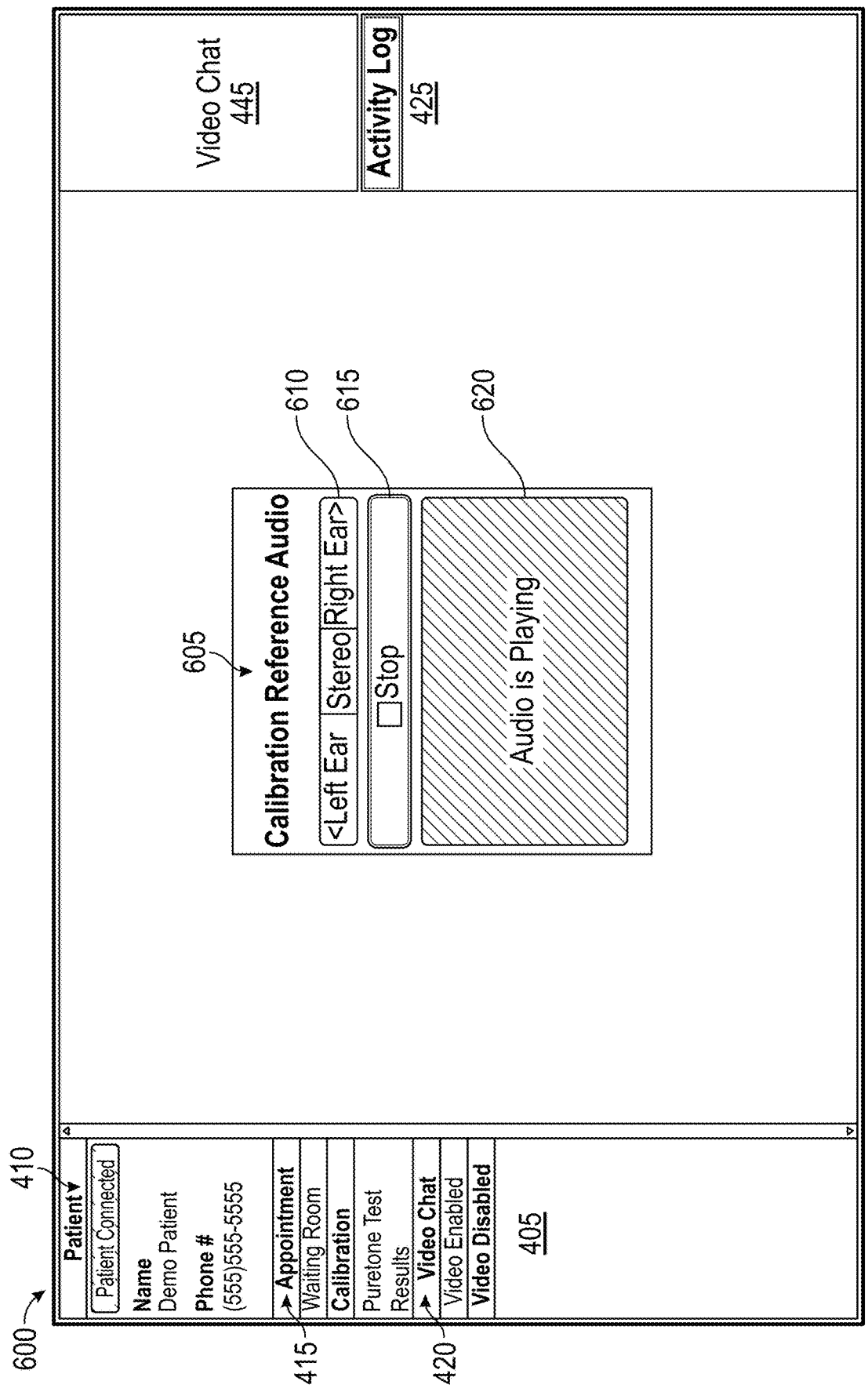
FIGS. 6A-6C are example GUIs for calibrating audio for a hearing test on a provider device, in embodiments.
Figure 6B:
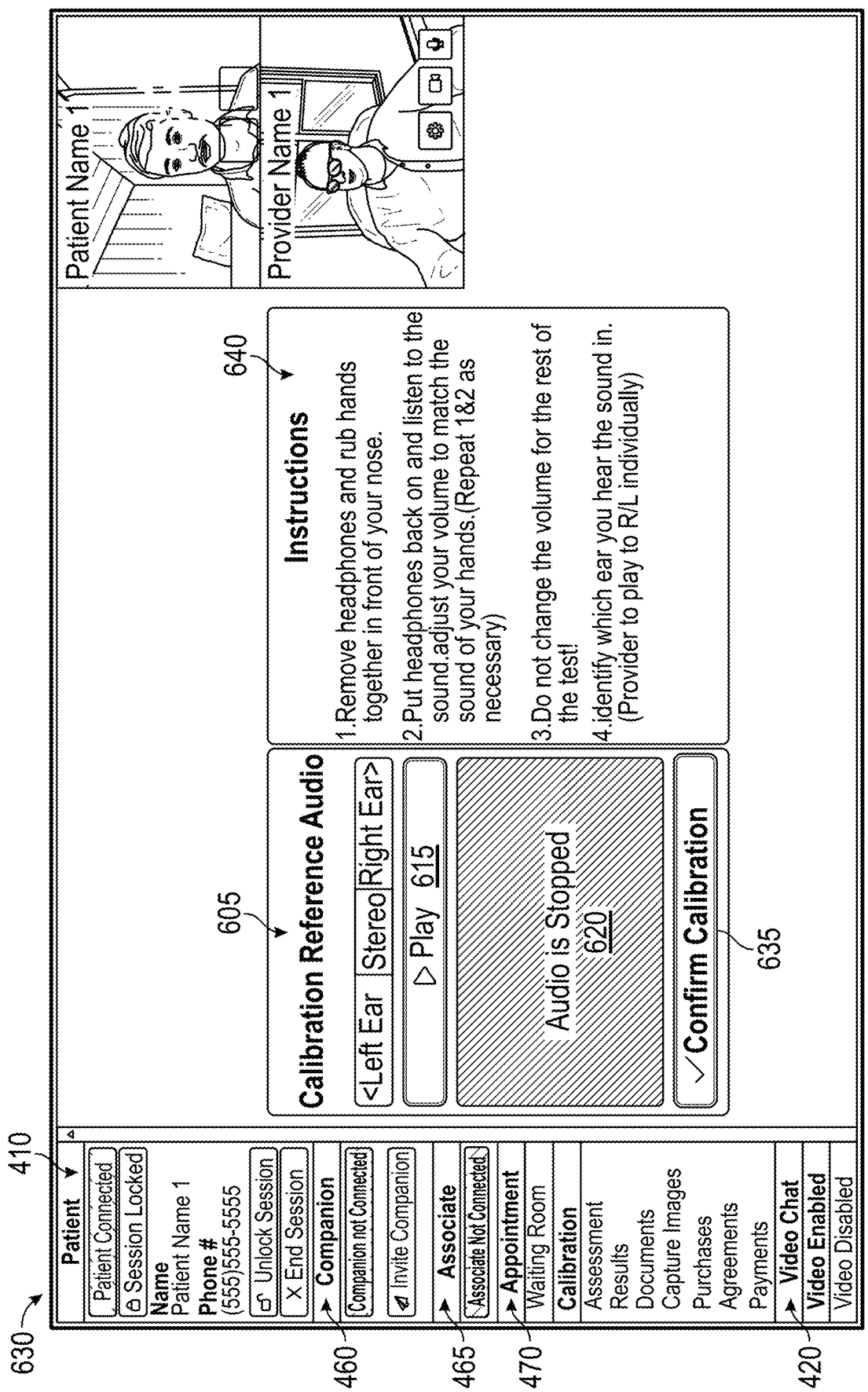

GUI 630 of FIG. 6B includes an additional example embodiment for a calibration GUI that may be displayed on a provider device. The GUI 630 may include a confirm calibration button 635 to confirm, upon selection of the button 635 by the provider, that calibration was completed. Selection of the button 635 may automatically navigate to the next step in the appointment tab 470 (e.g., assessment). The GUI 630 also includes written instructions 640 for performing the calibration, which the provider may use to as reference for calibration, or may read to a patient to help the patient with calibration.

Figure 6C:
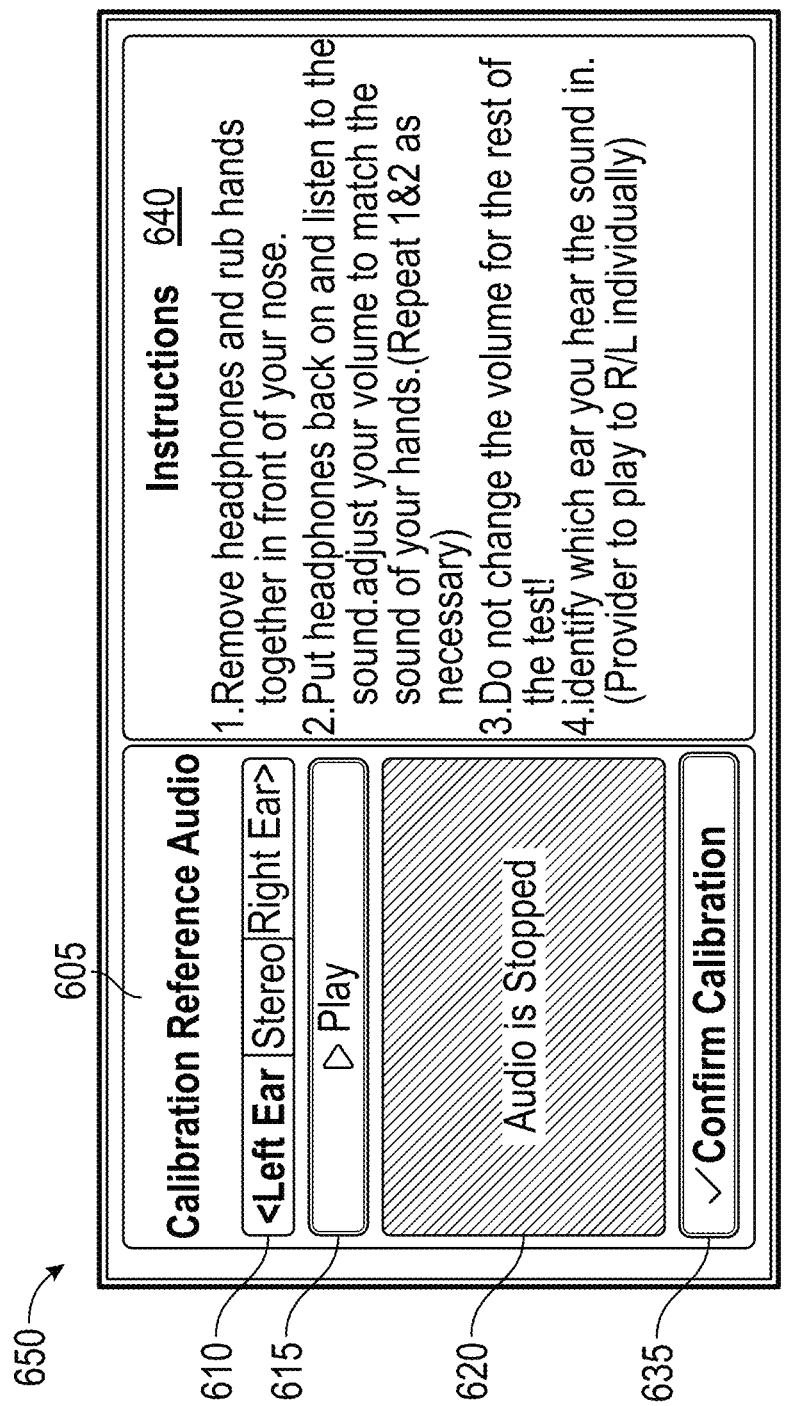

GUI 650 of FIG. 6C shows an example of a portion of the GUI 630, wherein the button 635 indicates that calibration has been confirmed (e.g., indicating that the provider has selected the button 635). The indicator 620 of FIGS. 6B and 6C further shows an example of what the indicator 620 looks like when the reference audio used for calibration is not being played.

Figure 7A:
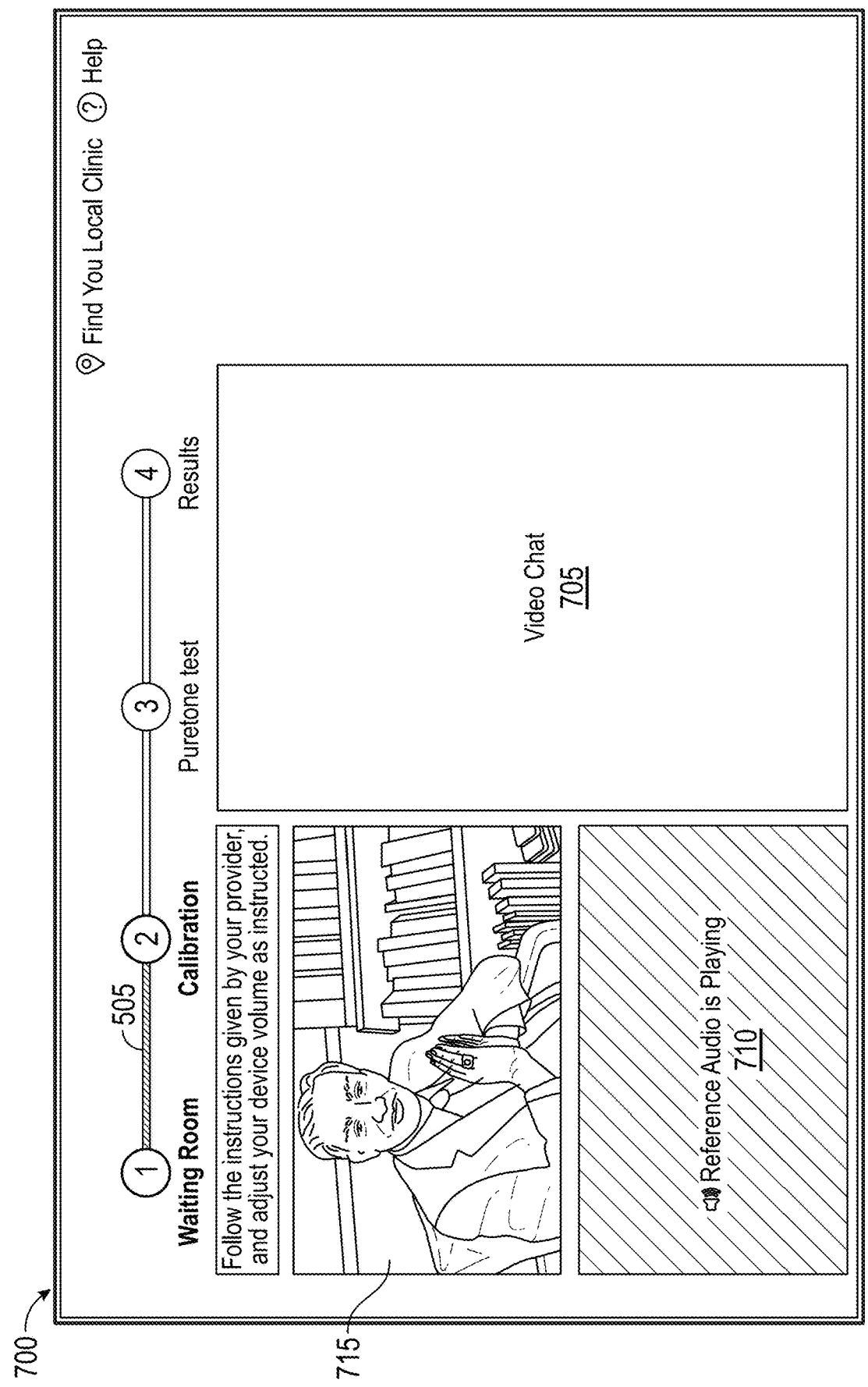
FIGS. 7A and 7B are example GUIs for calibrating audio for a hearing test on a patient device, in embodiments.

The GUI 700 of FIG. 7A shows in the status 505 that the appointment is in a calibration step. The GUI 700 also includes video chat 705 so the patient can see the provider and/or a guest in the GUI 700. An indicator 710 indicates that calibration audio is or is not being played. In the example of FIG. 7A, audio is currently playing, which may be indicated by color and/or text in the indicator 710. The indicator 710 may be helpful because, if a patient has hearing loss, they may not realize when the sound is playing and that they need to adjust the volume up to be able to hear the calibration audio. A video 715 may show a patient how to generate reference audio (e.g., rubbing hands together, rubbing two pieces of paper together) to compare to calibration audio being controlled by the provider. The patient can then adjust the volume of their speaker(s) until the calibration audio being controlled by the provider matches the reference audio being generated by the patient. This calibration is indicated by an operation 225 of the method 200.

Figure 7B:
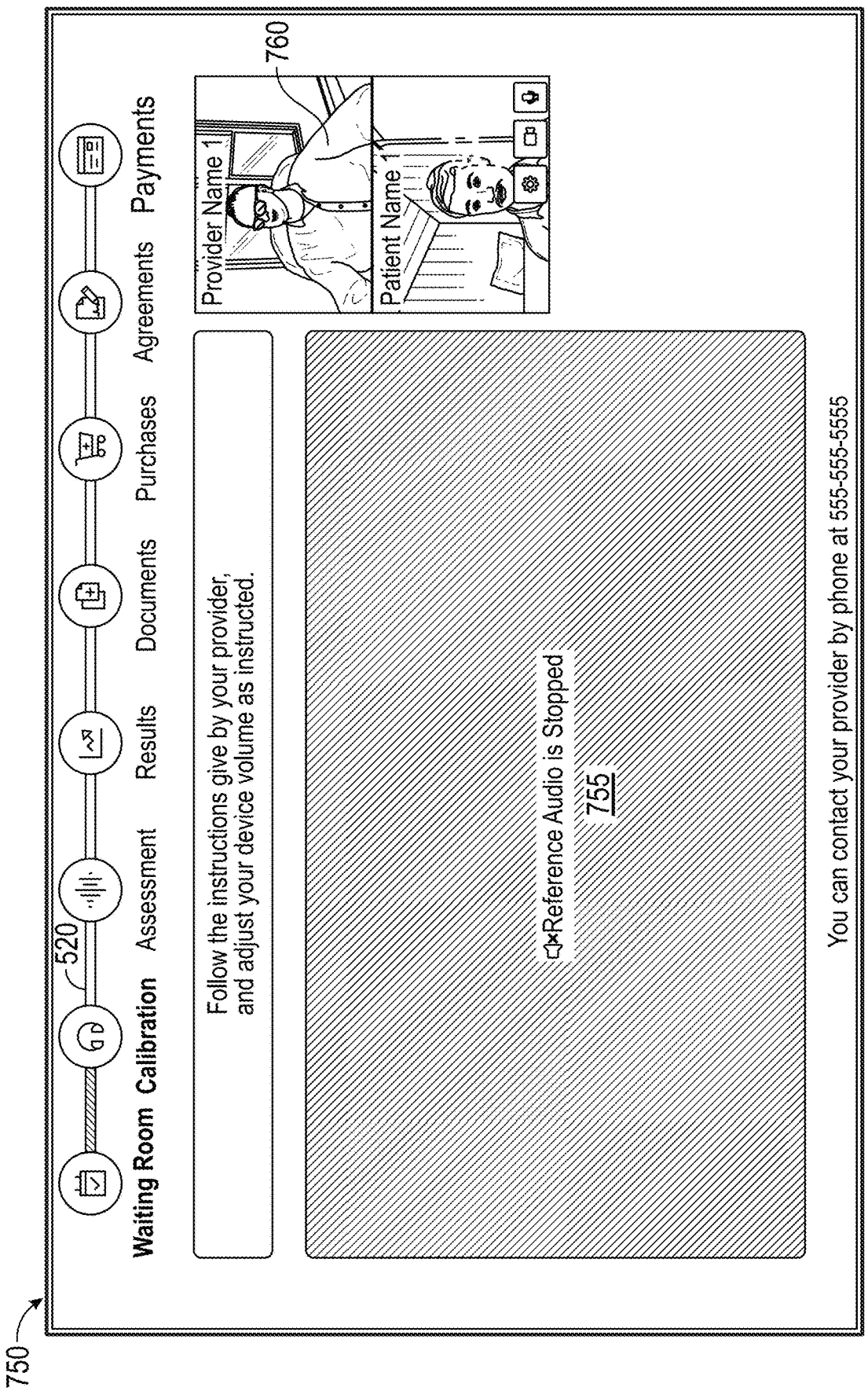

GUI 750 of FIG. 7B shows another example of a GUI that may be displayed on a patient device during calibration of audio. The status 520 may indicate that the session is currently in a calibration step. The GUI 750 further includes a video chat 760 showing the provider and patient (and may additionally show an associate and/or guest in other embodiments). Further, the GUI 750 includes an indicator 755 that may function similarly to the indicator 710 of FIG. 7A.

Figure 11A:
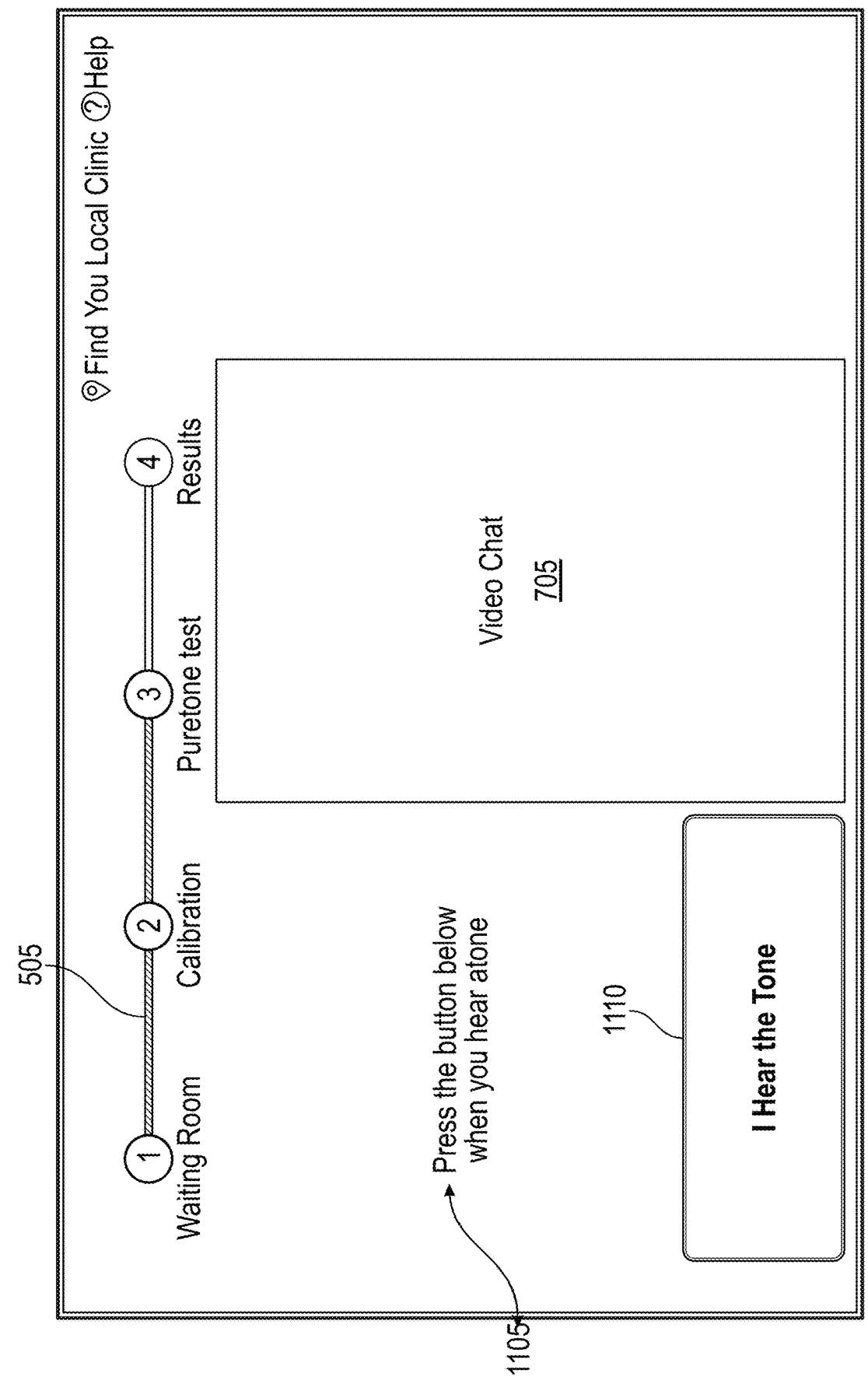
FIGS. 11A and 11B are example GUIs for a patient to confirm a tone has been heard during a hearing test on a patient device, in embodiments.
Figure 11B:
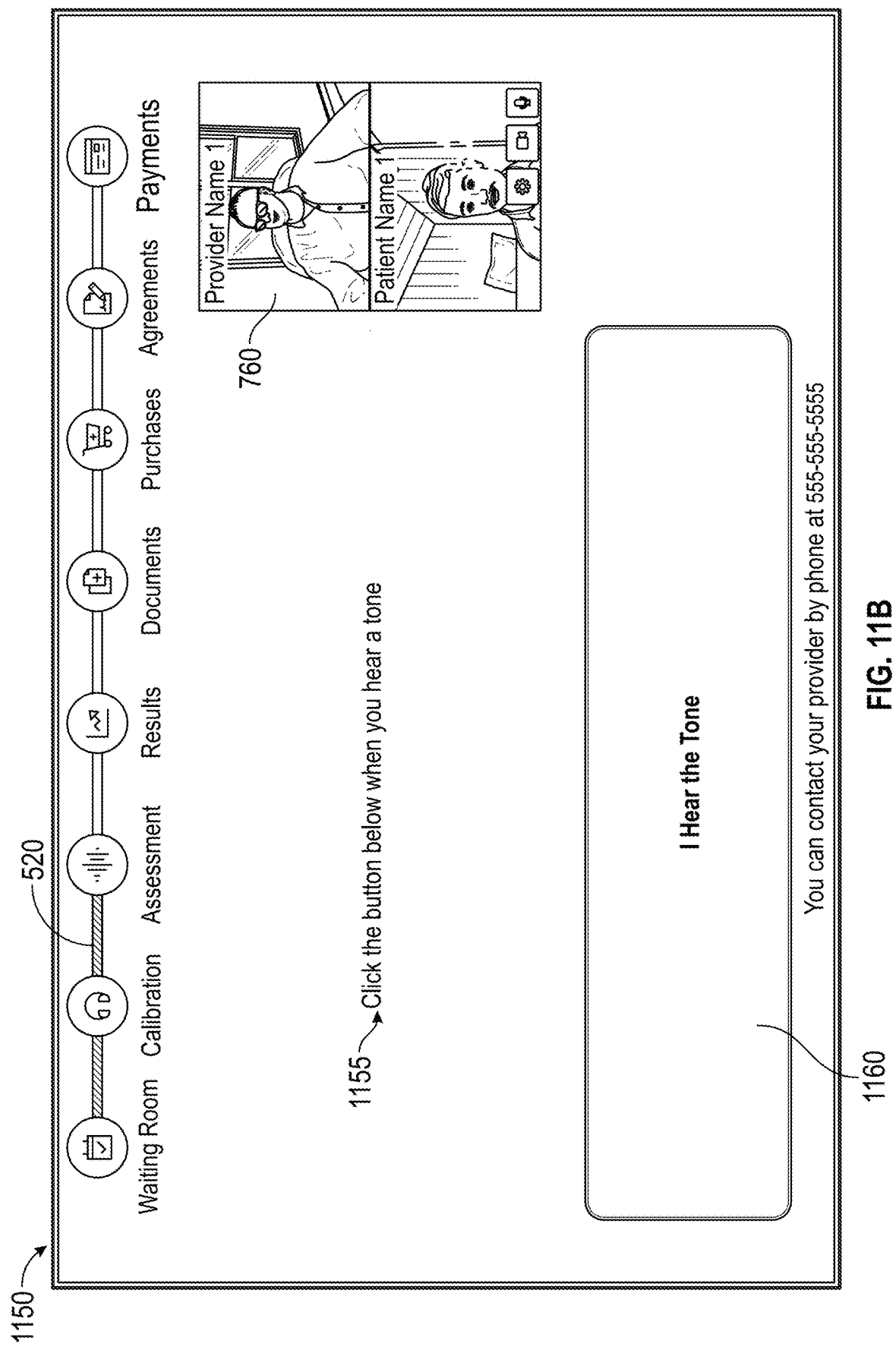

In an operation 230 of the method 200, the hearing test is administered by the provider. GUIs for the provider device for administration of the hearing test are shown in FIGS. 8A, 8B, 9, and 10 and an example GUI for the patient device of administration of the hearing test is shown in FIGS. 11A and 11B.

Figure 8A:
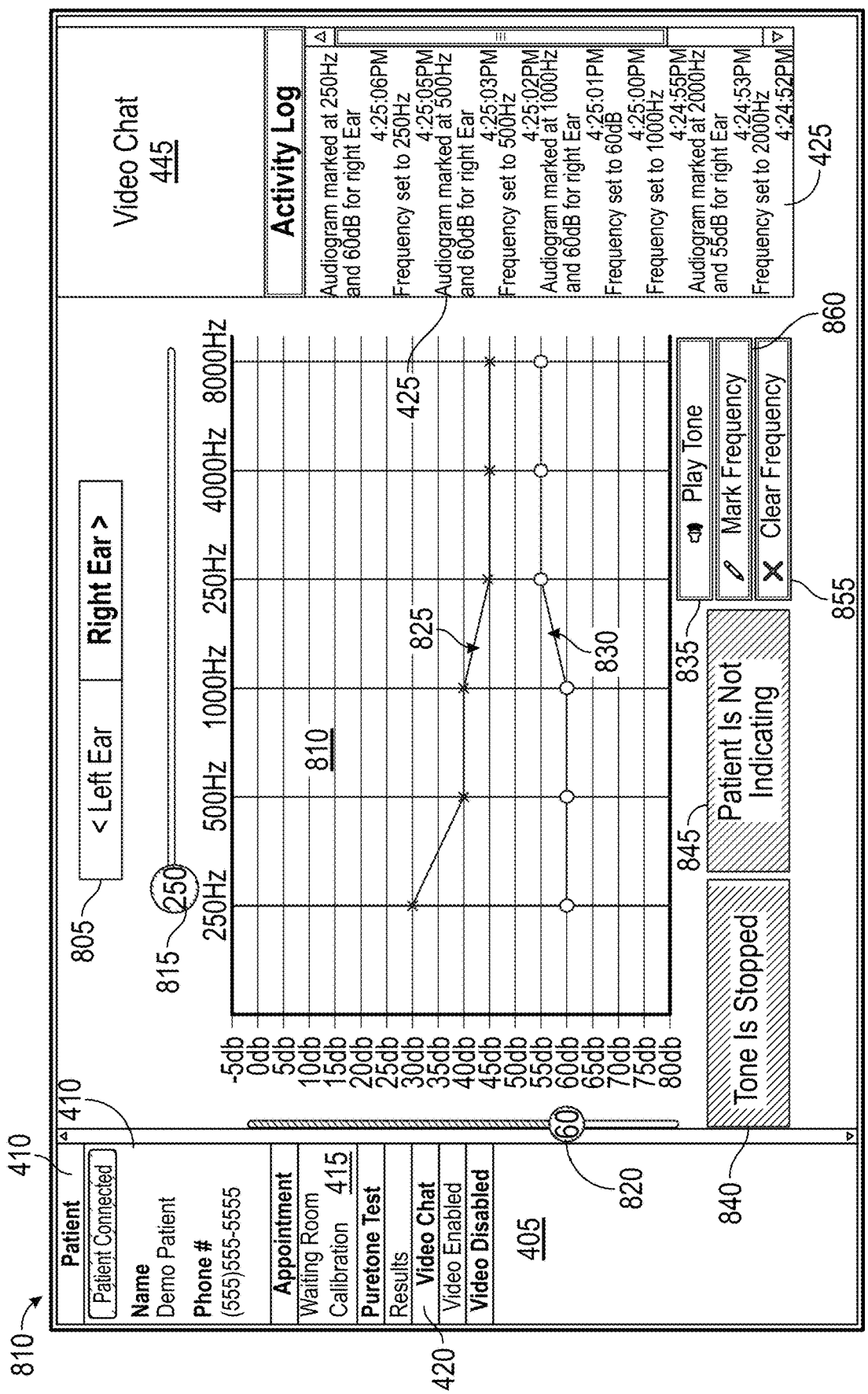
FIGS. 8A and 8B are example GUIs for administering a hearing test on a provider device, in embodiments.

A GUI 800 of FIG. 8A shows a completed example audiogram 810 for a patient. Button 805 may be selected by the provider to control which ear sounds are being played to and for which ear data is being entered into the audiogram 810. Slider button 815 may be moved to different frequencies to control what frequency ear sounds are being played and for which frequencies data is being entered into the audiogram 810. Similarly, slider button 820 may be moved to different loudness (e.g., decibel) levels to control what volume ear sounds are being played and for what volume data is being entered into the audiogram 810. In the example GUI 800, the activity log 425 has data in it because the hearing test has been completed. The activity log 425 records all activity that occurred during the hearing test and timestamps associated with each activity (e.g., when sounds are played and at what volume and frequency levels, when places on the audiogram are marked). In various embodiments, the activity log 425 may also be user stamped for each action or item in the activity log 425. In other words, each action or item logged may also be associated with a user (e.g., the provider, the patient, sales representative, financing person, receptionist/intake employee). In this way, the activity log 425 may also record who has taken each action.

A button 835 allows the provider to play a currently selected tone on the patient device. An indicator 840 indicates whether audio is currently being output by the patient device or patient device browser. An indicator 845 indicates whether the patient has selected a user interface element (e.g., button) indicating that they have heard a sound. A button 860 allows the provider to mark a spot on the audiogram 810 for a just played sound, and a button 855 allows the provider to clear a mark on the audiogram that for a currently selected location on the audiogram.

Figure 8B:
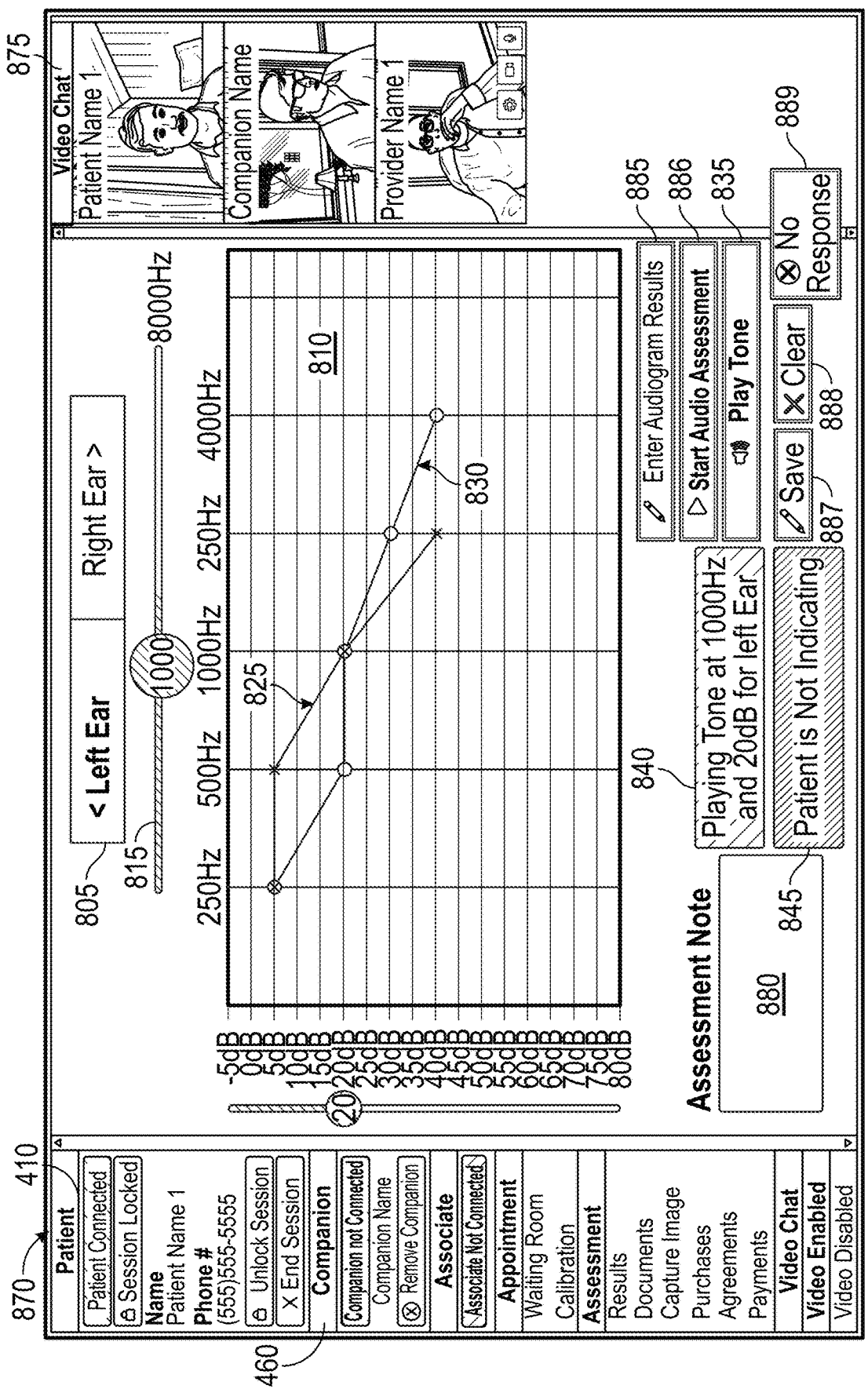
Figure 9:
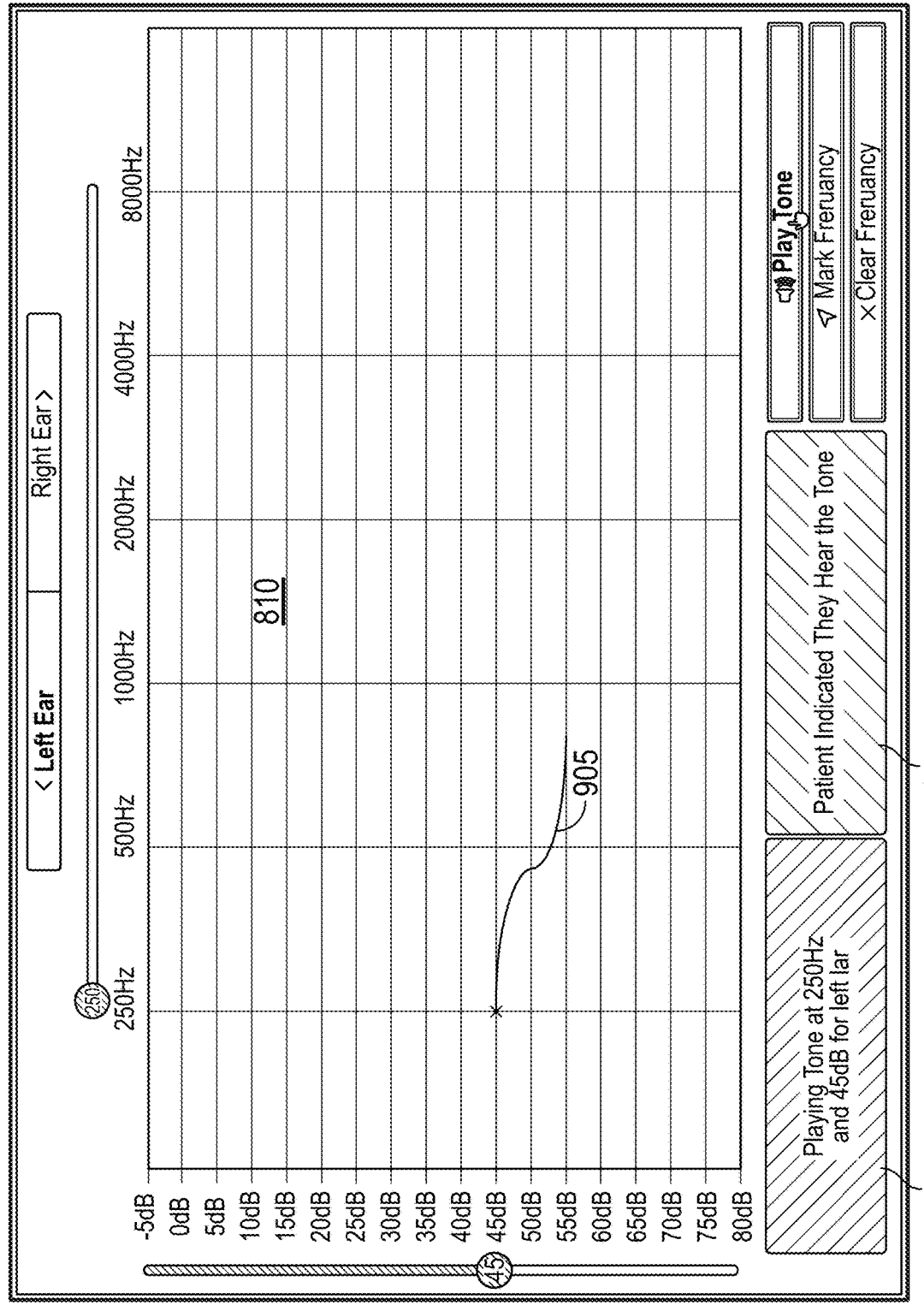
FIG. 9 is an example GUI for playing a tone during a hearing test on a provider device, in embodiments.
Figure 10:
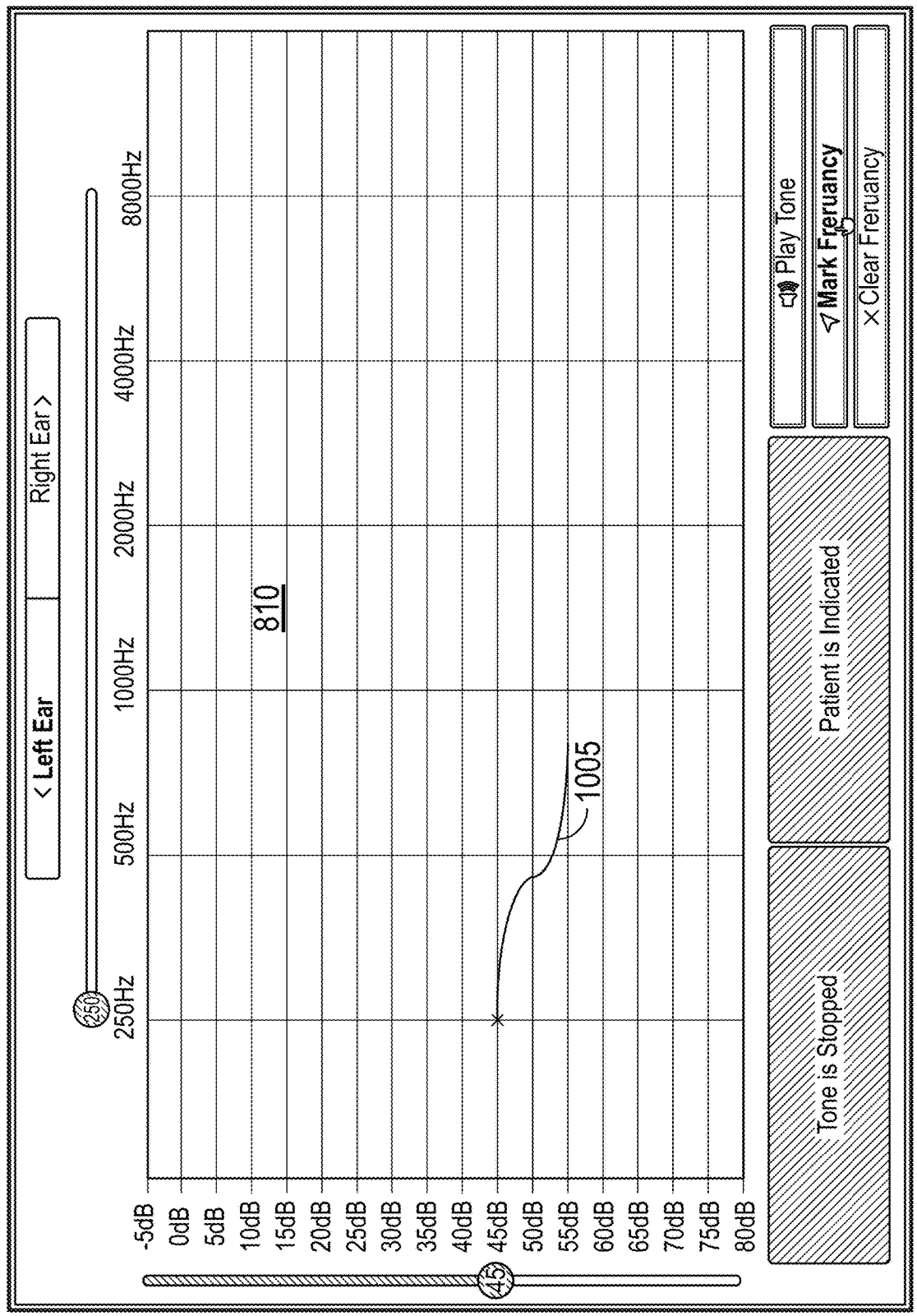
FIG. 10 is an example GUI for marking an audiogram during a hearing test on a provider device, in embodiments.

GUI 870 of FIG. 8B shows another example of a provider GUI for administering a hearing test. The GUI 870 includes a dialog 880 where a provider may enter notes about a hearing test as well as video chat 875, which includes video of a provider, companion, and the patient. Further, the GUI 870 includes a button 885 for entering audiogram results. The button 885 may be selected to allow the provider to manually mark the results in the audiogram 810. A button 886 may be used to start an automatic assessment. In an automatic assessment, portions of the hearing test may be automated. For example, the selection of and playing of different tones may be automated. In another example, placing marks in the audiogram 810 may be automated when the patient indicates they hear sound at the same time a tone is being played.

The GUI 870 further includes a button 887 for saving the results entered into the audiogram 810. The GUI 870 further includes a button 888 that may be used to clear one or all of the marks entered into the audiogram 810. The GUI 870 further includes a no response button 889, which may be used to indicate that a patient did not hear a sound at all for a particular tone being played.

The GUI 900 shows a portion of the GUI 800, but not as a completed audiogram. Instead, the GUI 900 shows an example where a 250 megahertz (MHz) and 45 decibel (dB) sound is being played for the patient. A faded "x" 905 shows the location on the audiogram currently selected by the provider for playing to the patient. The indicator 840 shows that audio is currently being output by the web application on the patient device. The GUI 1000 shows that a provider has marked the position on the audiogram with a solid "x" 1005 using the button 860. The provider may then select a new location on the audiogram to move on to a new sound to be played for the user. The example GUIs 900 and 1000 of FIGS. 9 and 10 may, in various embodiments, be used with either of the example GUIs 800 or 870 shown in FIGS. 8A and 8B.

The GUI 1100 of FIG. 11A illustrates what a patient may see during the hearing test. The GUI 1100 includes instructions 1105 and a button 1110 for the patient to press when they hear a sound. The patient may additionally communicate with the provider by speaking to the provider during the real-time communication facilitated by a server, web application, etc. When the patient presses the button 1110, the indicator 845 of the GUI 800 may change so the provider can see that the patient has indicate they can hear the noise. This data (that the patient pressed the button 1110) may also be recorded in the activity log 425 for recordkeeping that the patient heard the sound played. GUI 1150 of FIG. 11B shows another example of a GUI a patient may see during administration of a hearing test, which may include a status 520, a video chat 760, instructions 1155, and a hear tone button 1160.

At an operation 235 of the method 200, the provider may navigate to a documentation review between the provider and patient associated with GUIs 1200, 1215, 1240, 1250, and 1260 of FIGS. 12A-12E and 1300, 1310, 1330, and 1340 of FIGS. 13A-13D. The GUI 1200 shows what a provider may see during hearing test results and documentation review. The provider may cause both of the provider device to navigate to at least one of the GUIs of FIGS. 12A-12E and the patient device to navigate to at least one of the GUIs of FIGS. 13A-13D by selecting the "results" tab of the tab 415 in the GUI 800, for example.

The GUI 1200 includes different documents that may be reviewed with the patient and displayed as document 1210 and 1305. The document may be literature related to hearing loss, hearing loss products (e.g., hearing aids), or may be related to the test results themselves. For example, the provider may display the completed audiogram itself to discuss it with the patient. The GUI 1215 of FIG. 12B and GUI 1310 of FIG. 13B shows an example where a completed audiogram 1220 is shared with the patient as shown in audiogram 1315 in FIG. 13B. A button 1225 may be used to hide the audiogram 1220 from the patient. An audiogram 1230 tab may include selectable options for overlaying various graphics onto the audiogram 1220 that may be visible to the provider and the patient (and the companion if there is one), as shown in FIGS. 12C-12E, 13C, and 13D. A history tab 1235 may be used display a past completed audiogram overlaid onto the audiogram 1220. For example, in FIG. 12C, a historical past audiogram 1245 is shown on the audiogram 1220 to demonstrate how a patient's hearing has changed over time. Although an example is not shown, the historical audiogram 1245 may be displayed on the patient device as well.

Figure 12A:
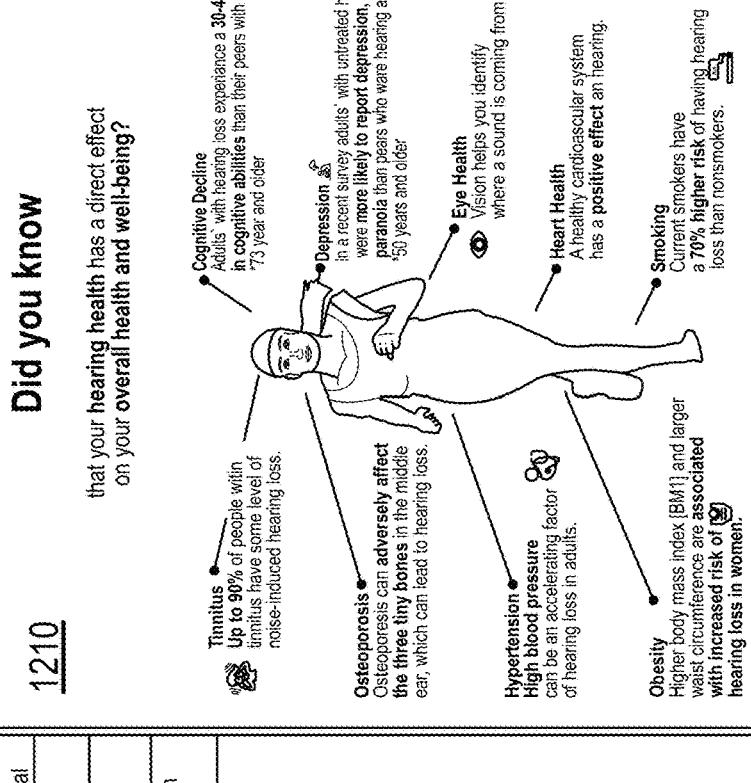
FIGS. 12A-12E are example GUIs for displaying hearing test results and documentation to a patient on a provider device, in embodiments.
Figure 12B:
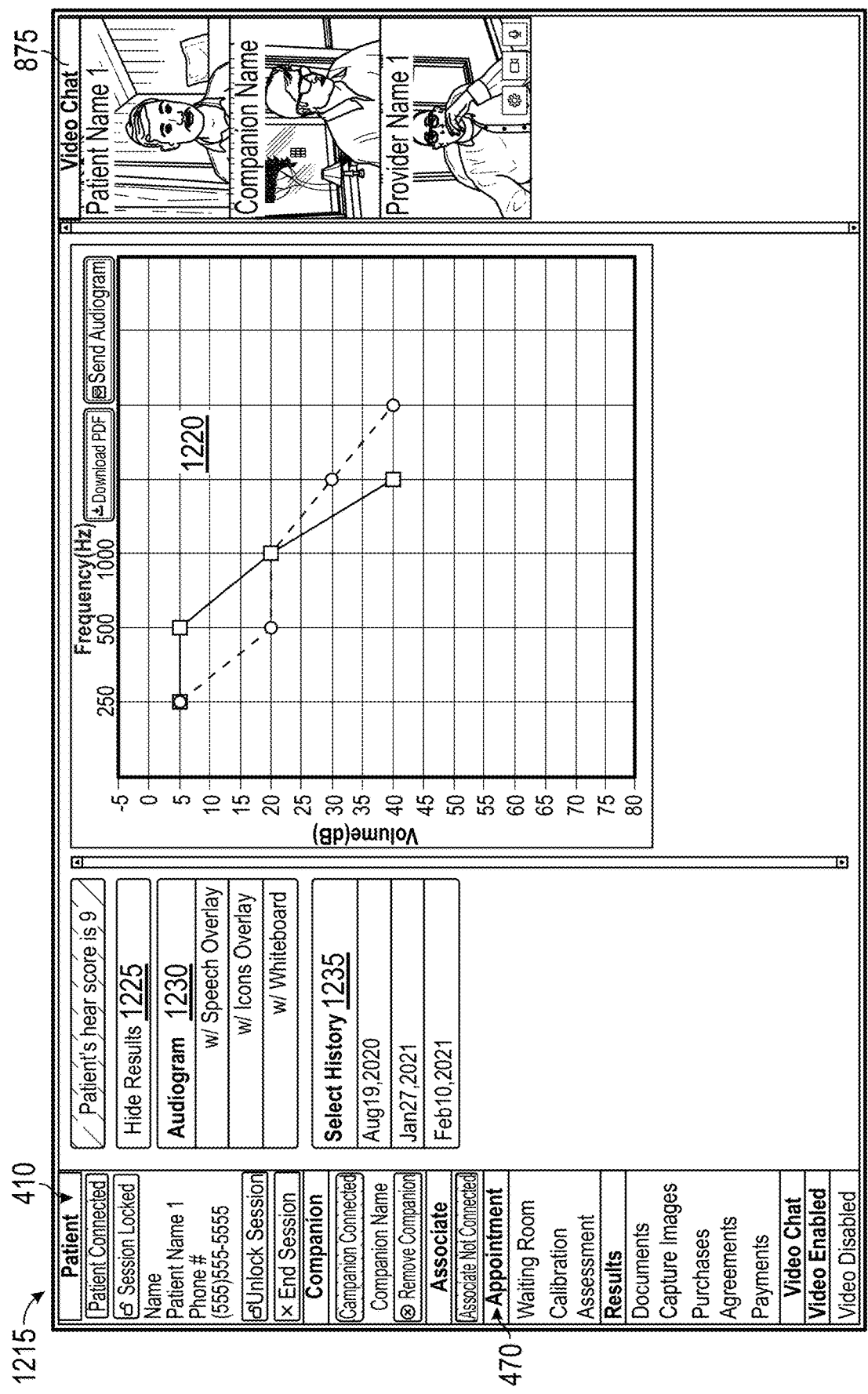
Figure 12C:
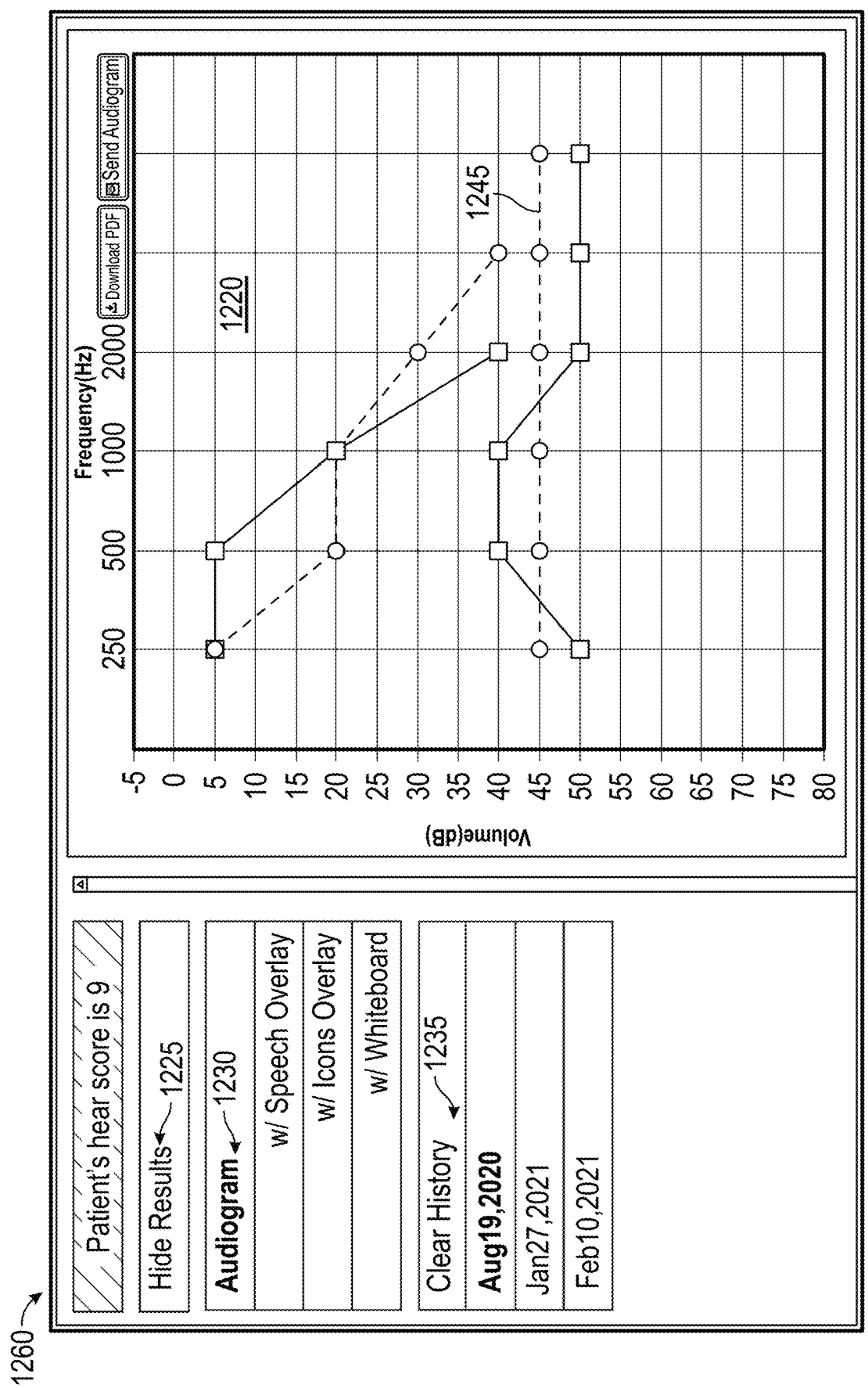
Figure 12D:
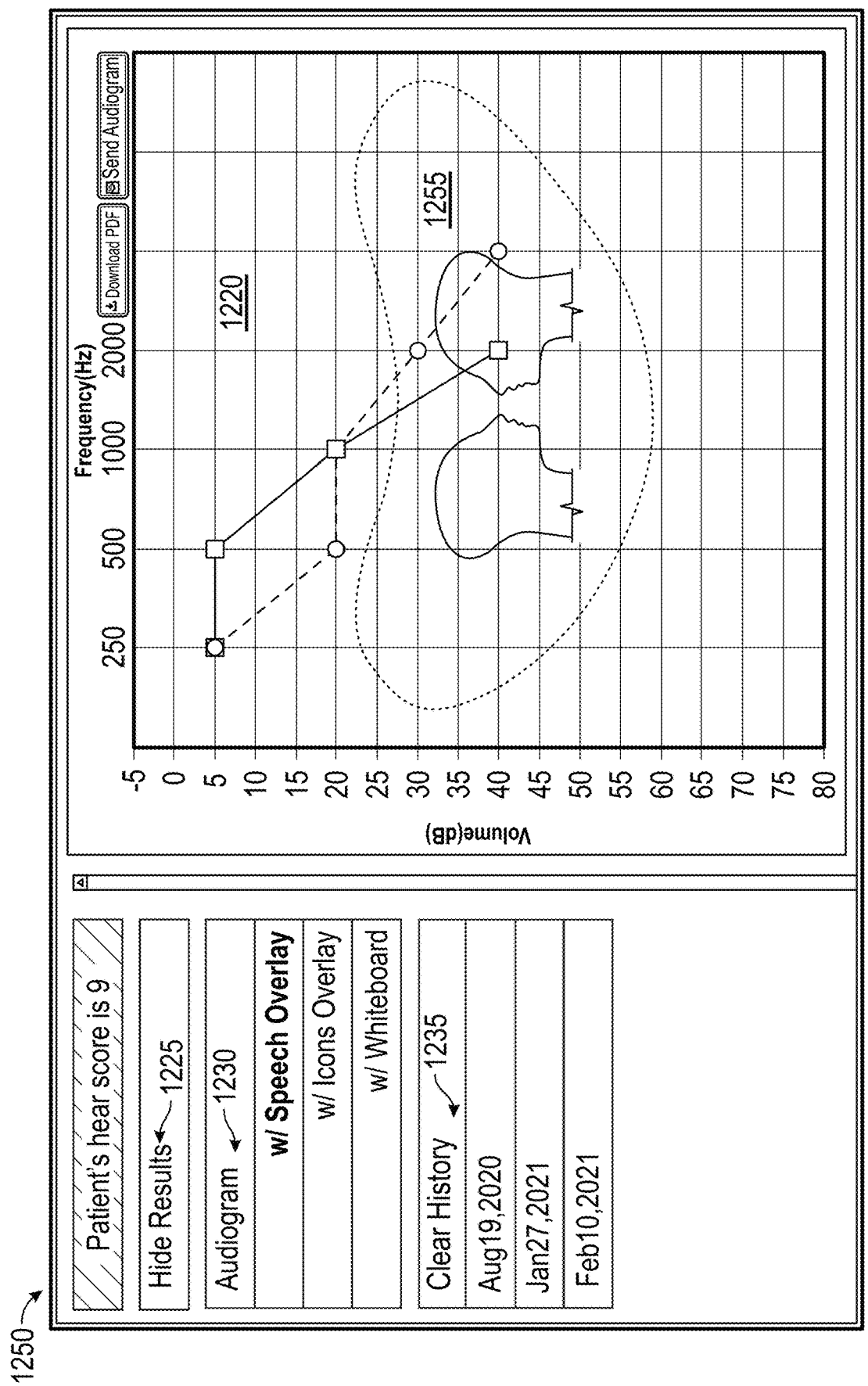
Figure 12E:
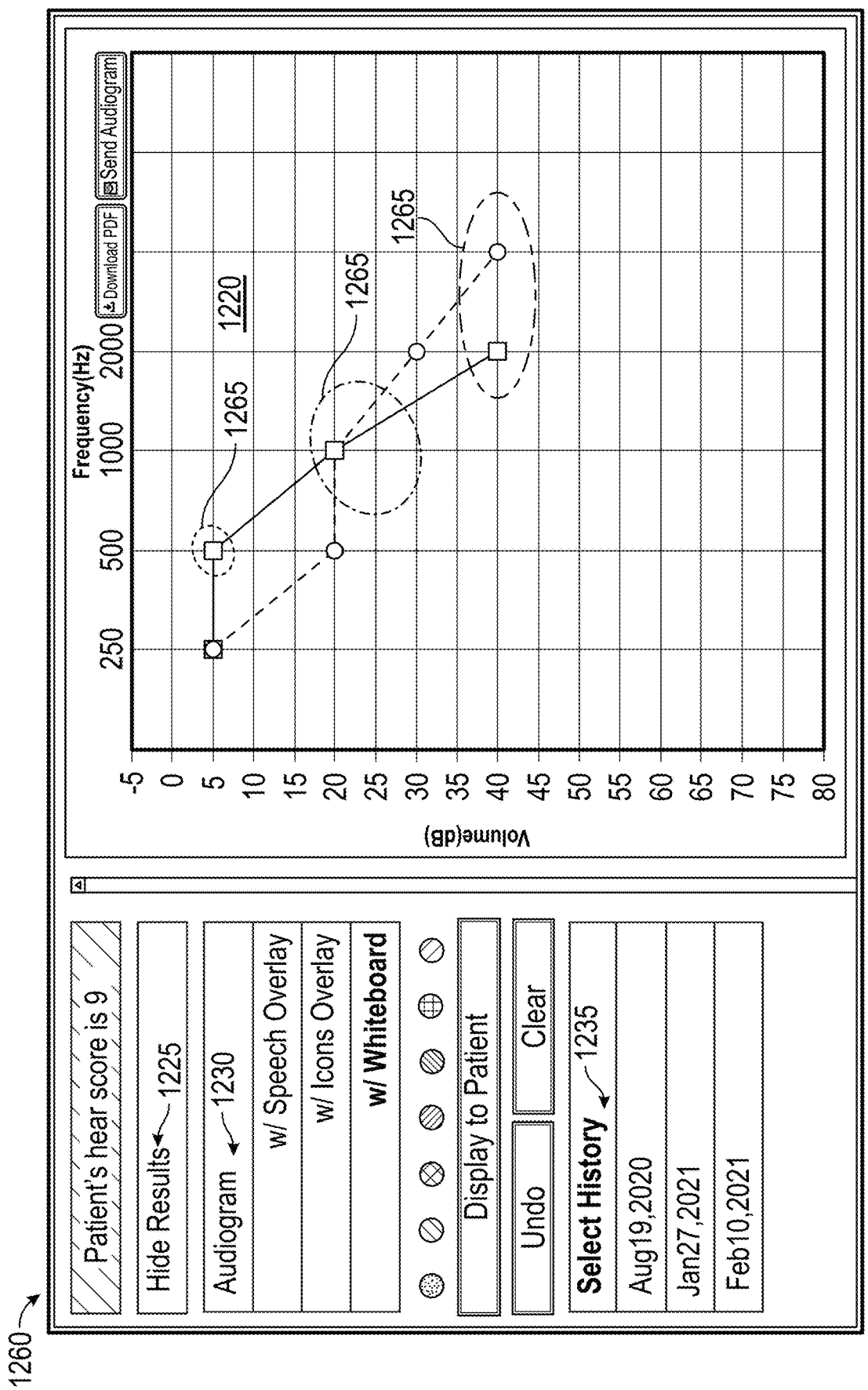
Figure 13A:
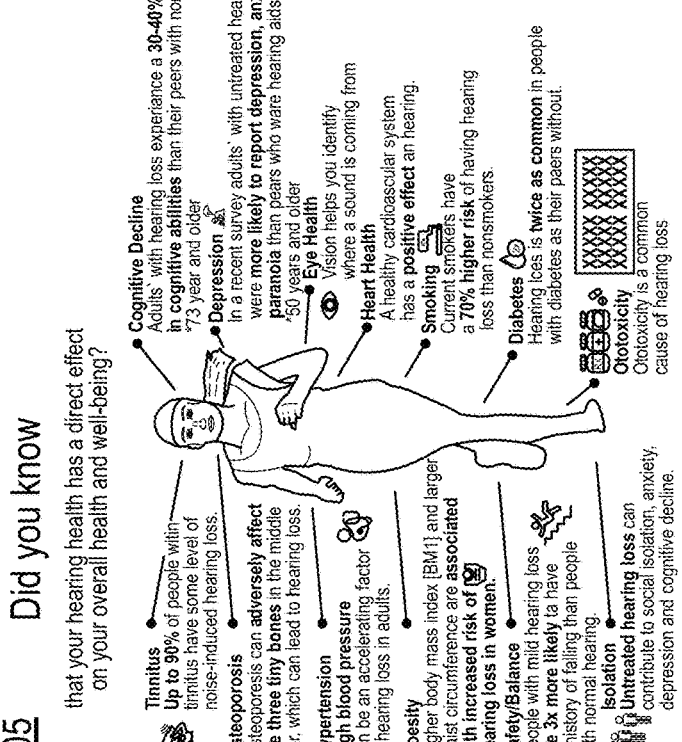
FIGS. 13A-13D are example GUIs for viewing hearing test results on a patient device, in embodiments.
Figure 13B:
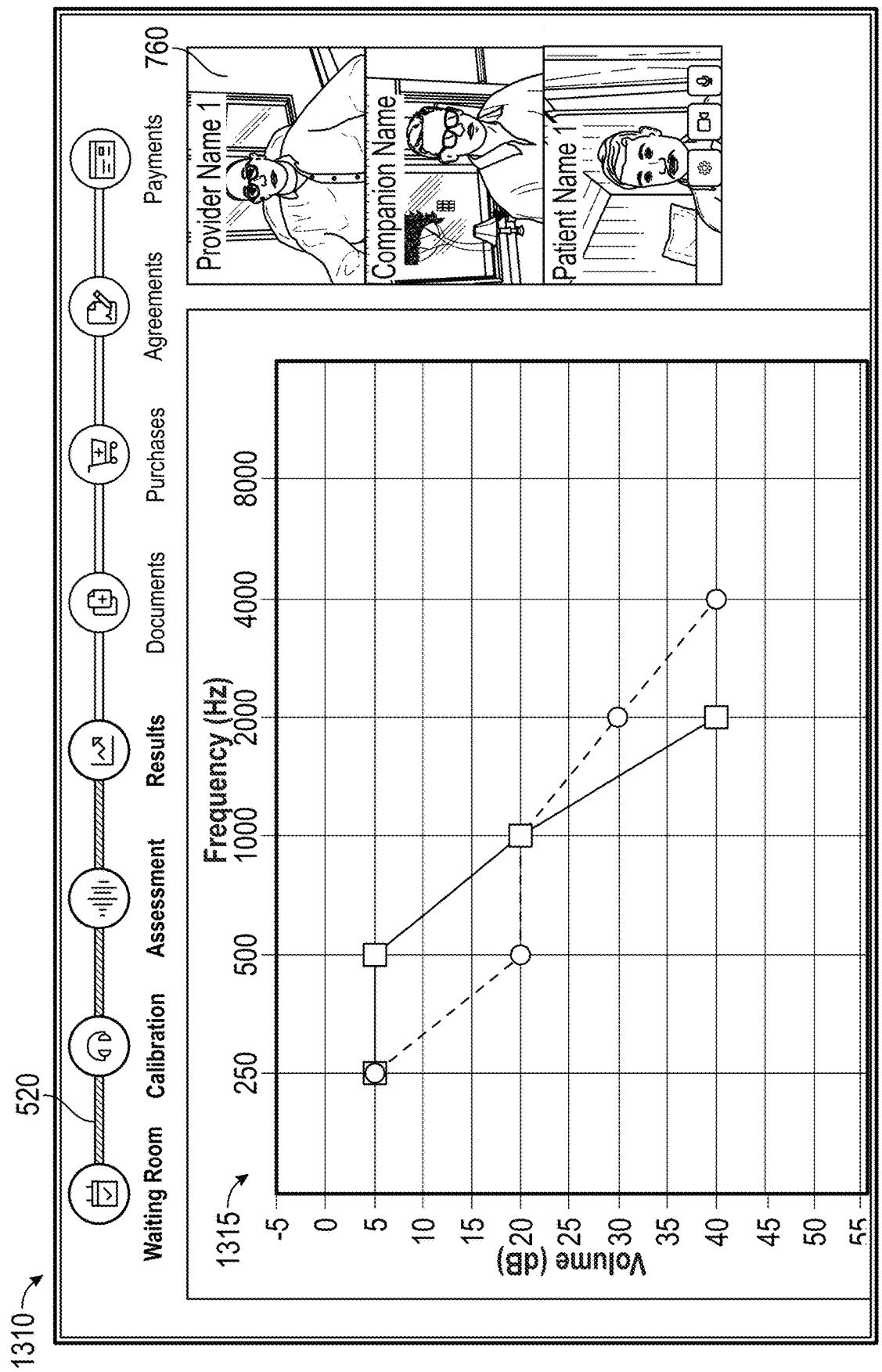
Figure 13C:
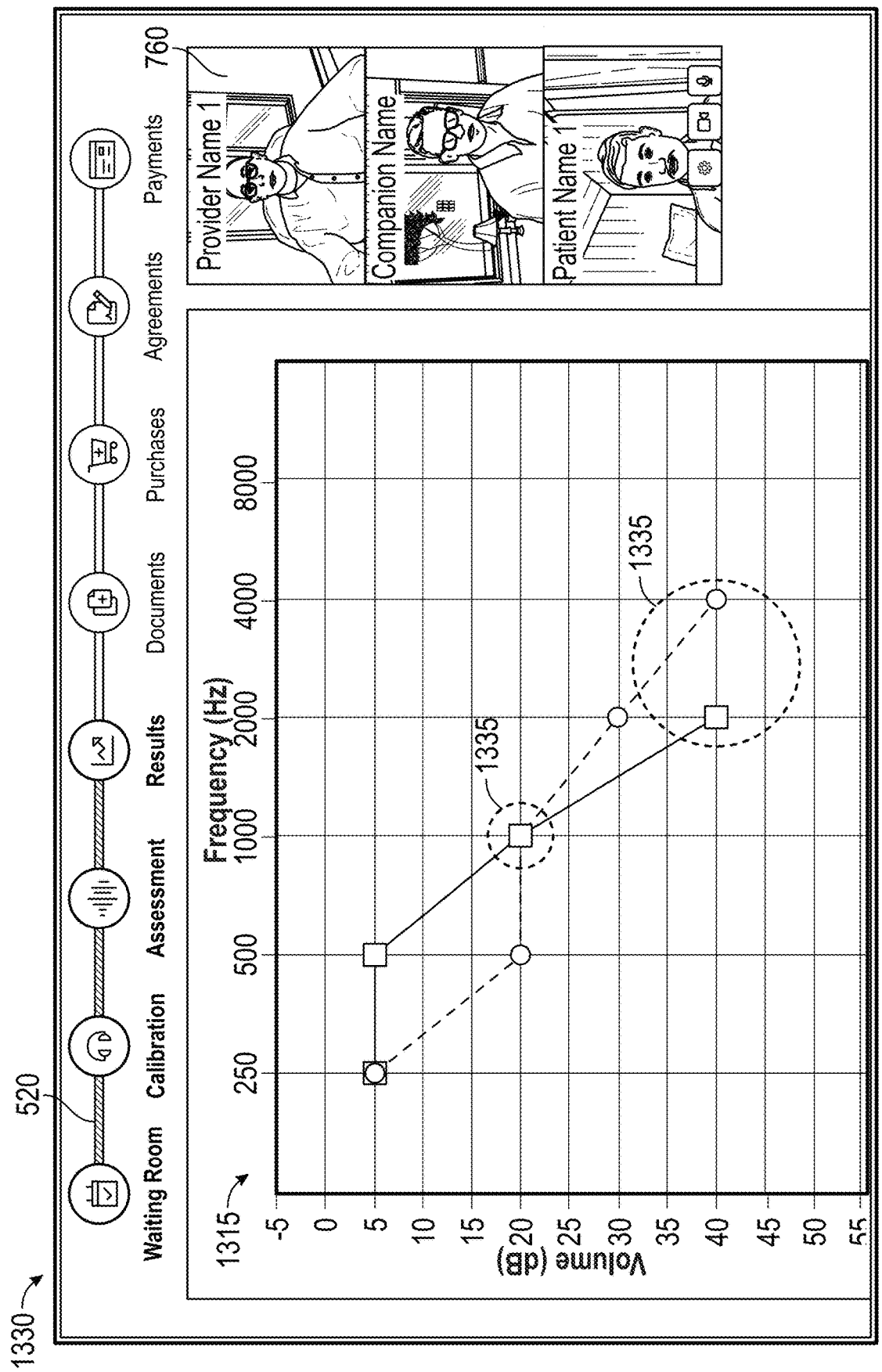
Figure 13D:
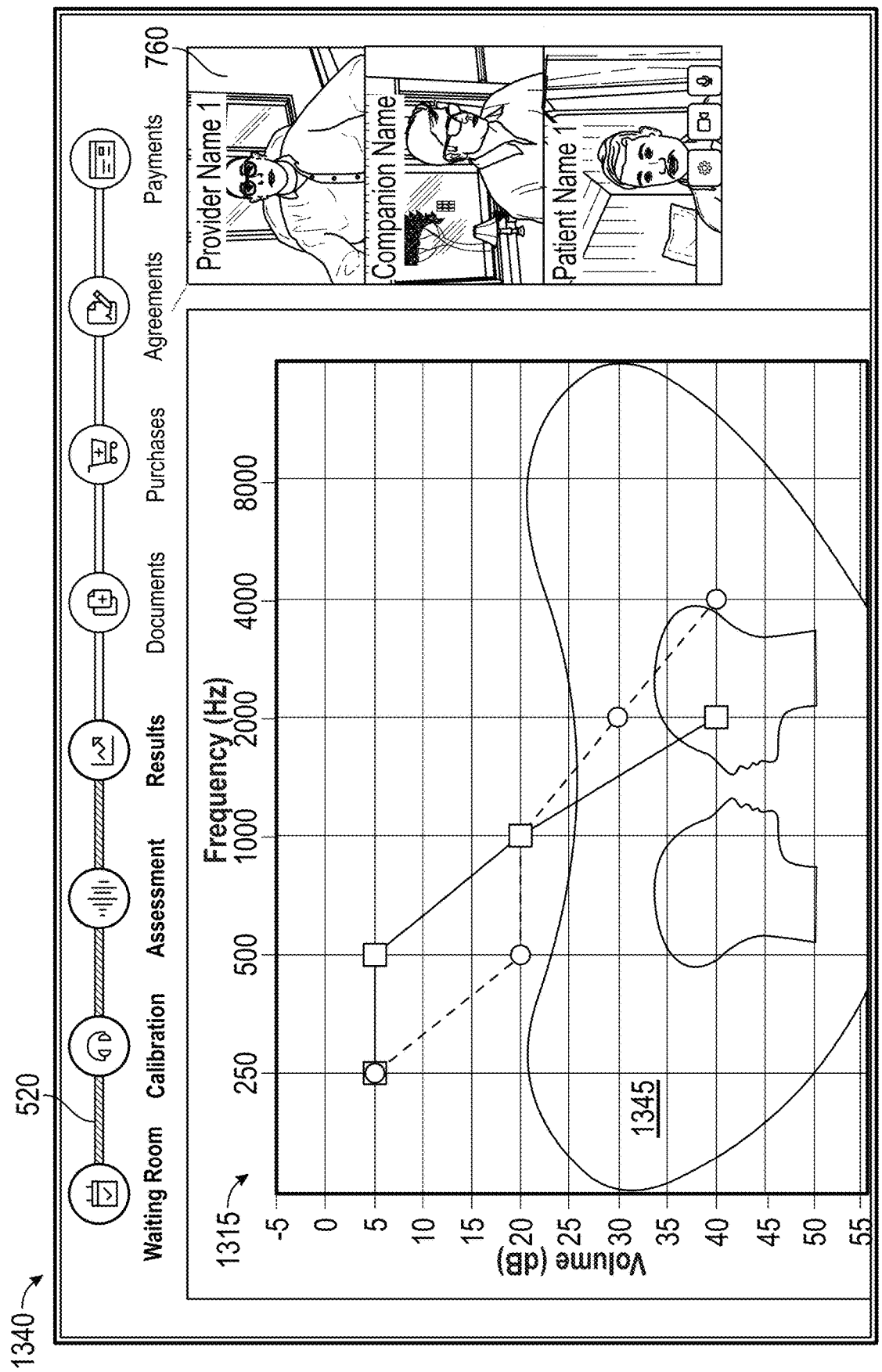

FIG. 12D shows an example of a speech overlay 1255 selected, which may be used to demonstrate to a patient (as shown in FIG. 13D as overlay 1345) the normal range of human speech. FIG. 12E shows a whiteboard or markup option selected in the tab 1230, where a provider may markup the audiogram (e.g., with markings 1265 of different colors, patterns, shapes, etc.) that the patient may see as shown in FIG. 13C as markups 1335.

FIG. 14 is an example GUI 1400 for displaying documentation on a patient device, in embodiments. As described above, the GUI 1400 may display a document 1405 that may be the same as a document selected by the provider. In FIG. 14, the document 1405 may be related to a hearing score that summarizes the results of the hearing test into an easy to understand scale or result for the patient (e.g., on a scale of 1-10).

Figure 15:
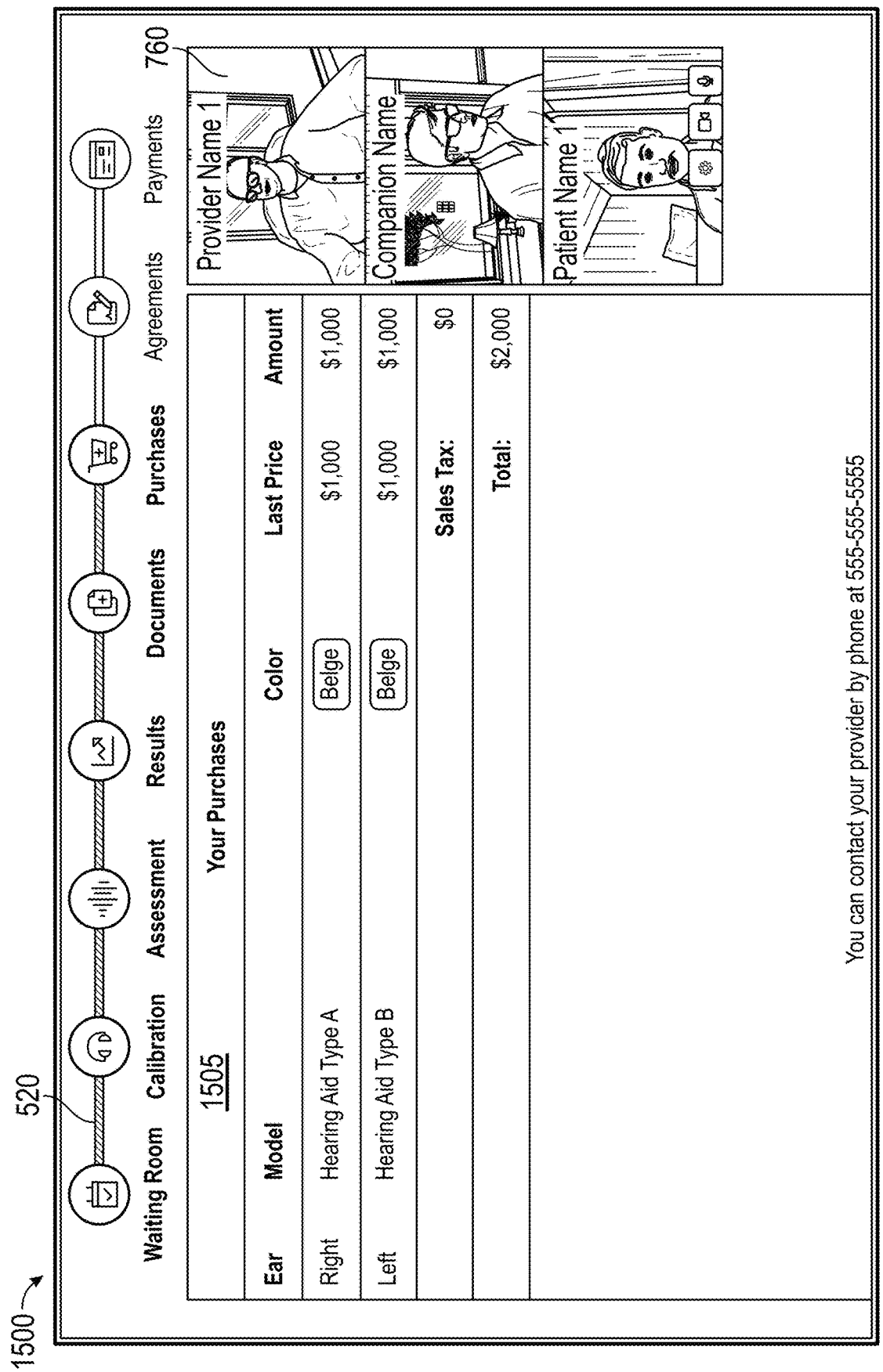
FIG. 15 is an example GUI for displaying purchase information on a patient device, in embodiments.

FIG. 15 is an example GUI 1500 for displaying purchase information 1505 on a patient device, in embodiments. The purchase information 1505 may be related to, for example, hearing aid devices the patient would like to purchase after learning the results of their hearing test. The purchase information 1505 may also correspond to information entered by the provider at GUI 2000 of FIG. 20. FIG. 20 is an example GUI 2000 for entering and displaying purchase information on a provider device, in embodiments. In the GUI 2000 the provider (or an associate) may enter information relating to specifications for hearing aid devices in dialog 2005, and that information may be summarized in a dialog 2010. The information in the dialog 2010 may be shared with the patient, for example, by selecting a toggle 2015.

Figure 16:
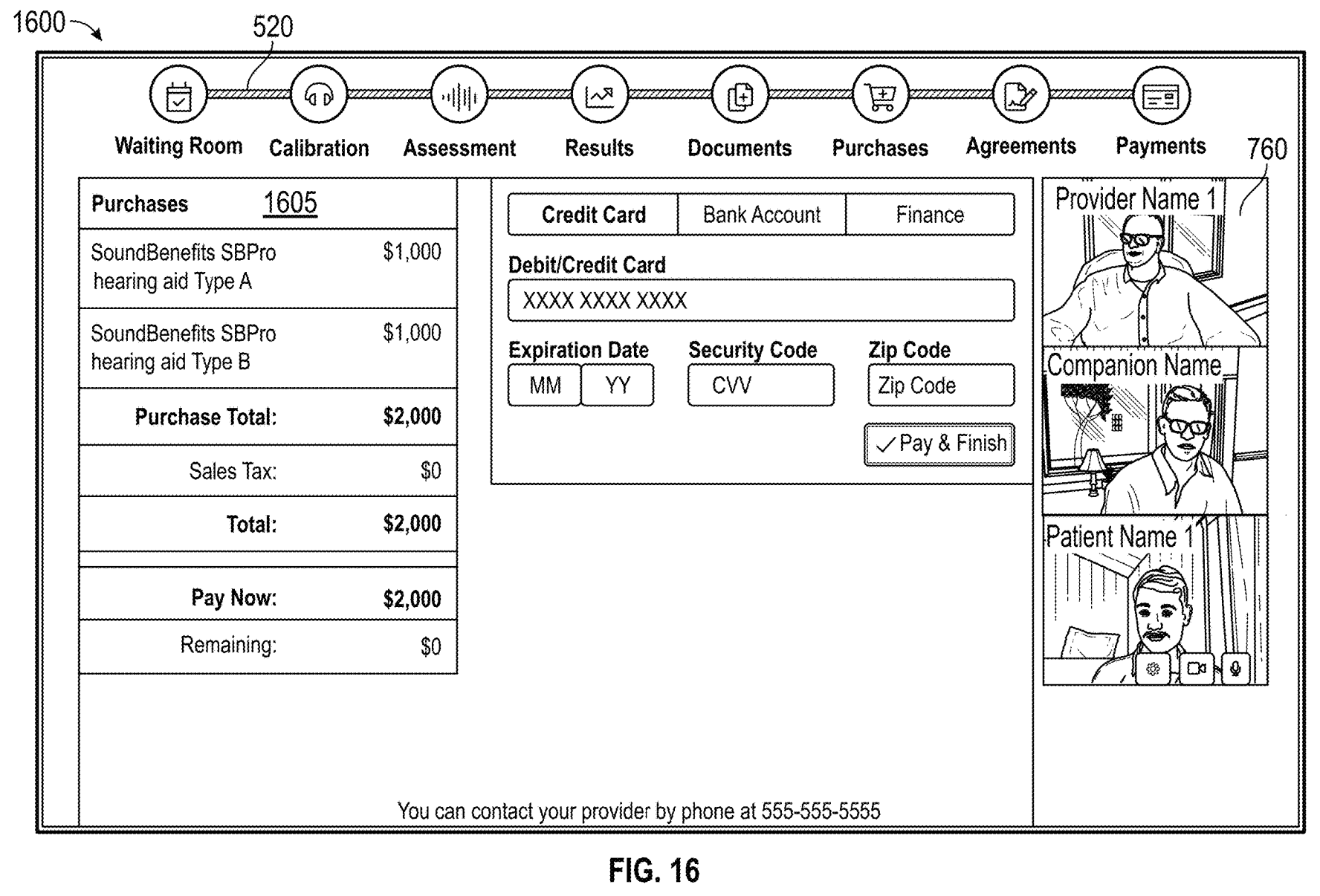
Figure 17:
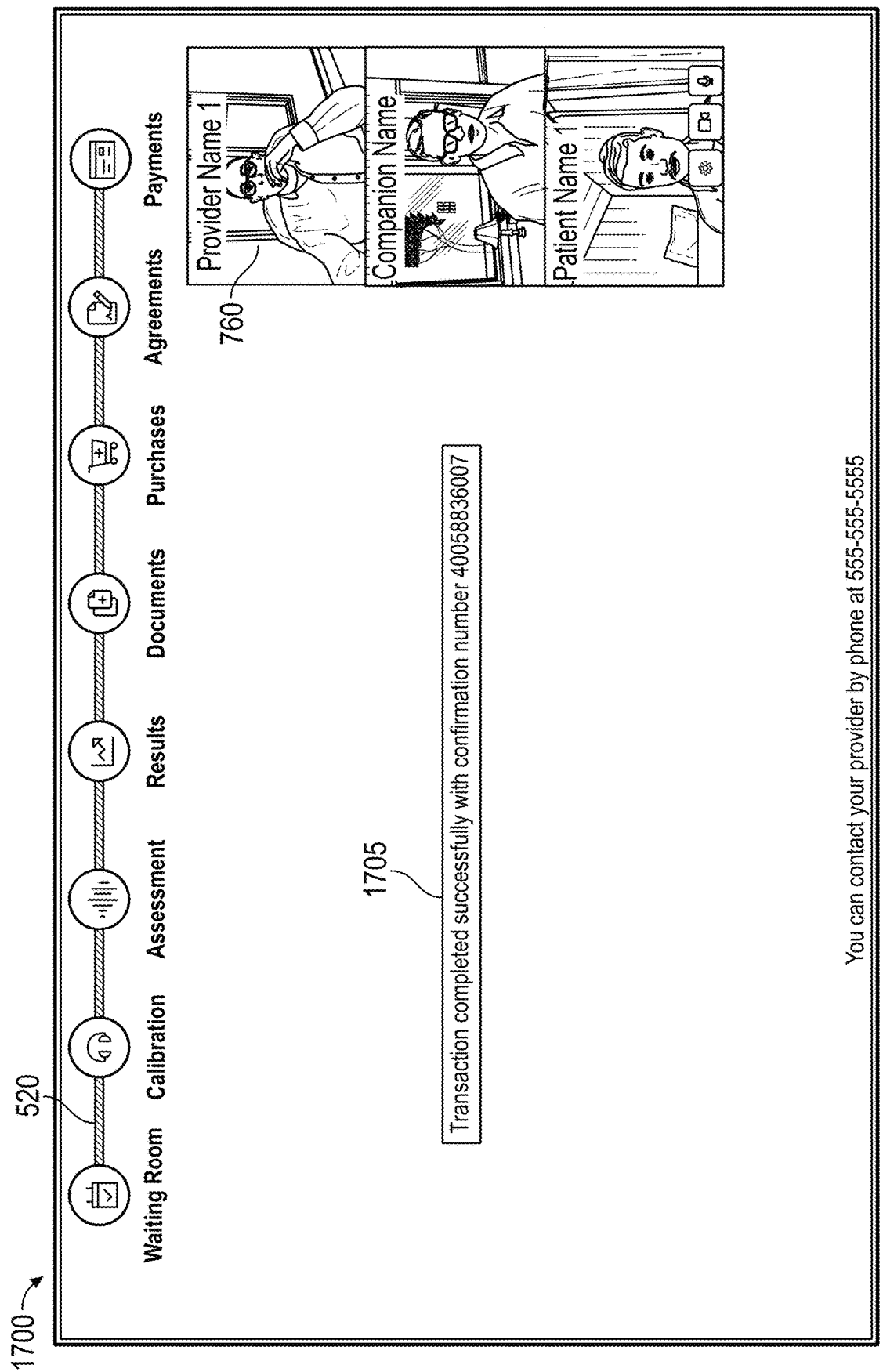
FIG. 17 is an example GUI for displaying purchase confirmation information on a patient device, in embodiments.

FIG. 16 is an example GUI 1600 for entering purchase information on a patient device, in embodiments. For example, the patient may enter credit card or other information in a dialog 1610 for paying for hearing aids or other devices or services agreed to and summarized in a dialog 1605. FIG. 21 is an example GUI 2100 for sending purchase information to a patient and/or guest device, in embodiments. The final purchase information 2105 may be send to a patient using a dialog 2110 for display in the GUI 1600. A toggle 2115 may be used to send payment information to a patient device so that the patient will pay, while a toggle 2120 may be used to send payment information to a companion or guest device so that the guest may pay. FIG. 22 is an example GUI 2200 for displaying purchase confirmation information 2205, 2210, and 2215 on a provider device when a patient or guest has actually paid for hearing aids or other devices or services, in embodiments. FIG. 17 is an example GUI 1700 for displaying purchase confirmation information 1705 on a patient device, in embodiments.

Figure 18:
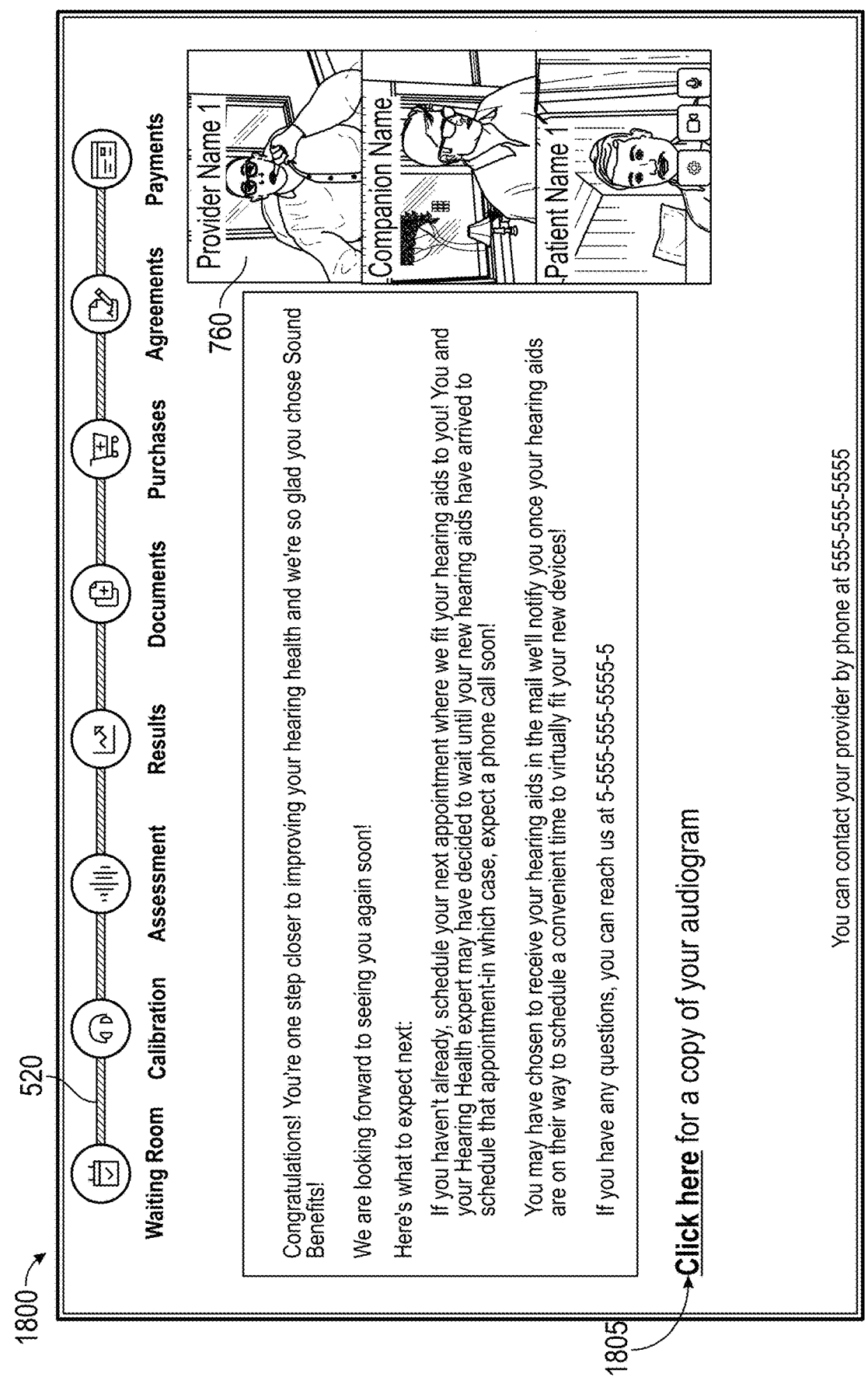
FIG. 18 is an example GUI for downloading a copy of hearing test results using a patient device, in embodiments.

FIG. 18 is an example GUI 1800 for downloading a copy of hearing test results using a patient device, in embodiments. The button 1805 may be used by the patient to download their audiogram to the patient device, which may or may not include any markups or other overlays shown to the patient during the review of the results with the provider.

Figure 19:
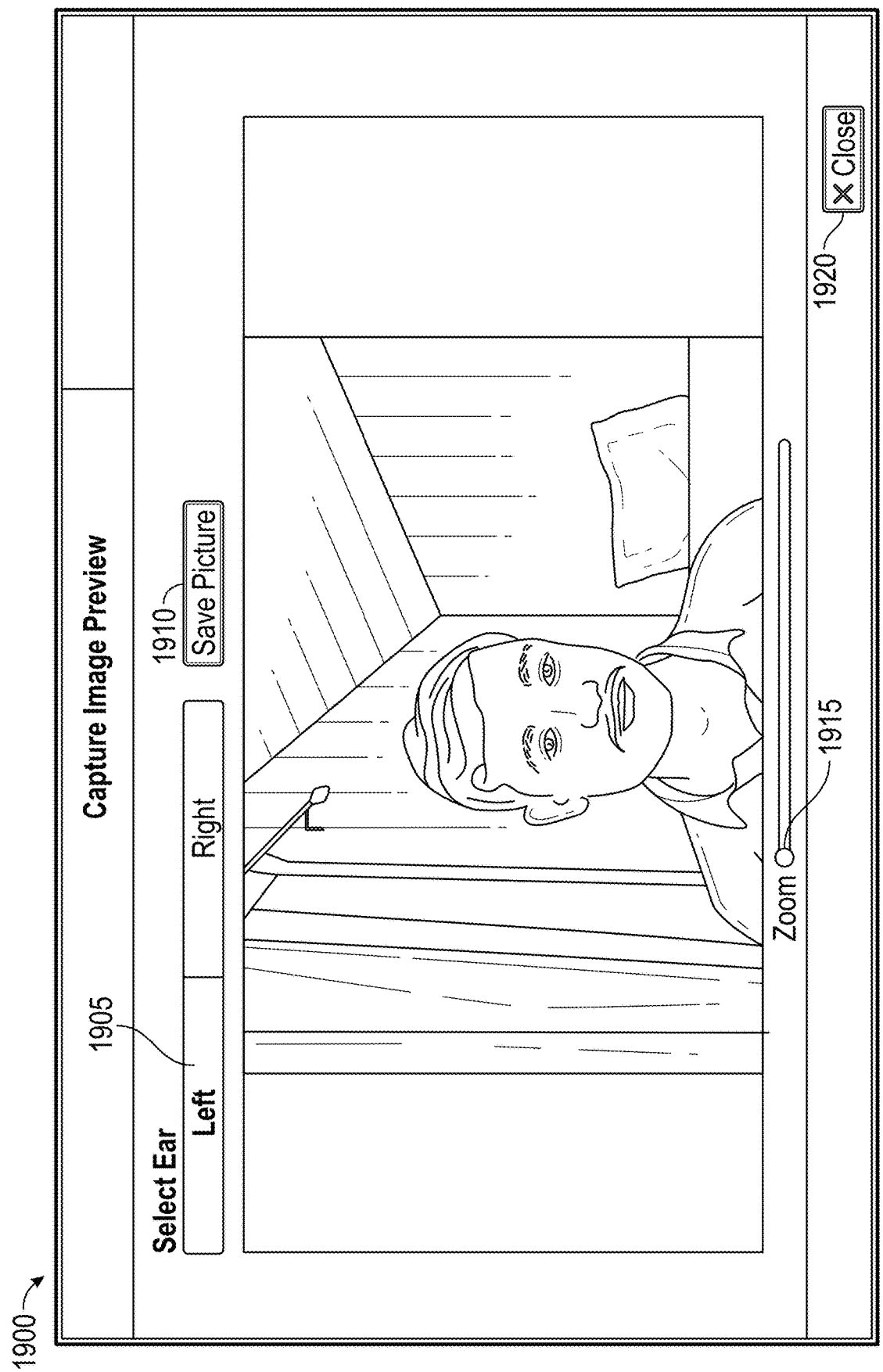
FIG. 19 is an example GUI for performing an image capture using a provider device, in embodiments.

FIG. 19 is an example GUI 1900 for performing an image capture using a provider device, in embodiments. In some embodiments, it may be helpful to estimate an ear size for sizing a hearing aid and/or a wire that is part of a hearing aid. The provider may capture an image using the GUI 1900, which shows video of the patient. An ear selection button 1905 may be selected by the provider to reflect which ear is being photographed, and a button 1910 may be used to save/capture an image. A slider 1915 may be used to zoom in or out on the patient, and the GUI 1900 may be closed (e.g., if it is pop up) using the button 1920.

Figure 24:
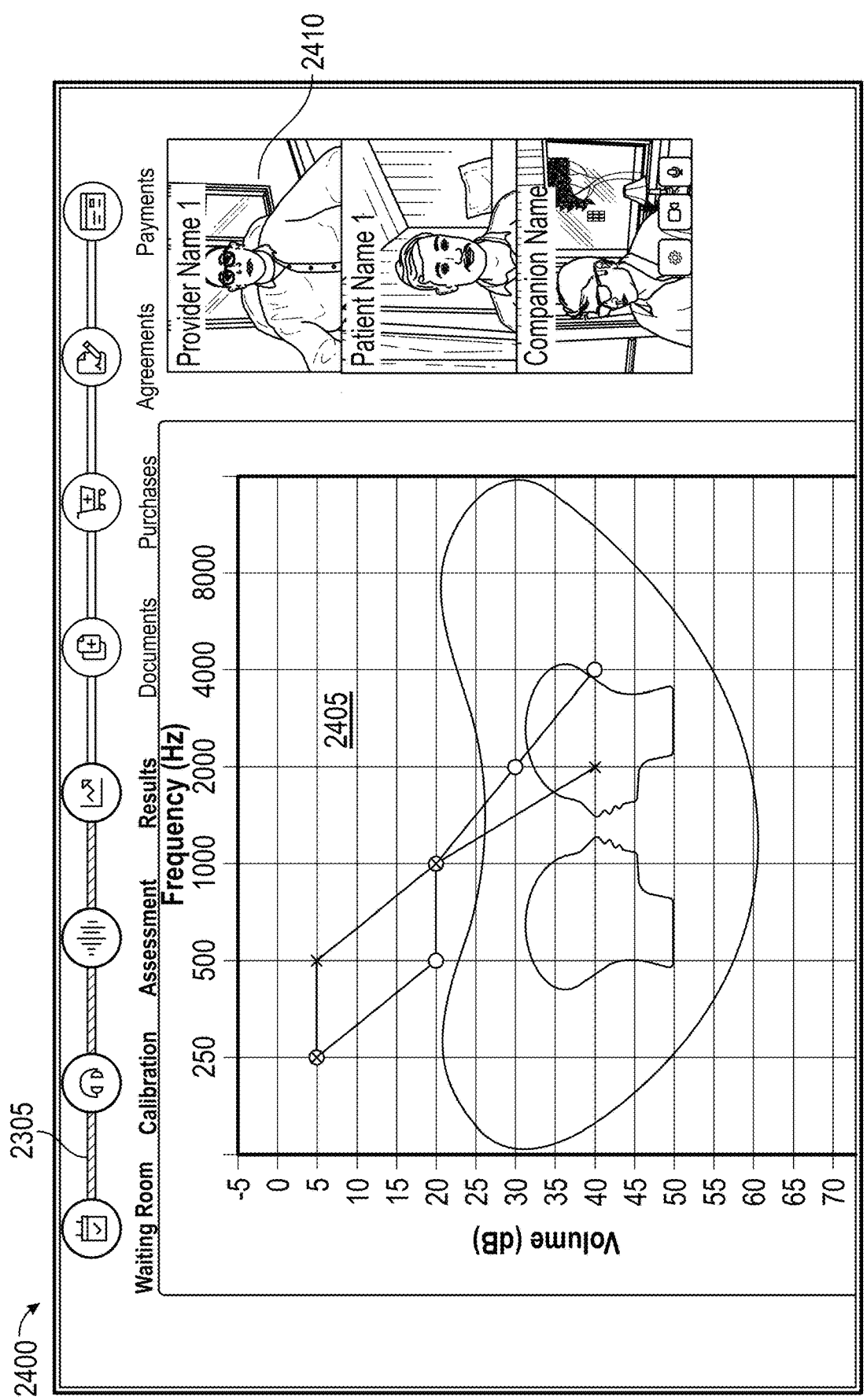
FIG. 24 is an example GUI for displaying hearing test results and documentation to a patient on a guest device, in embodiments.
Figure 25:
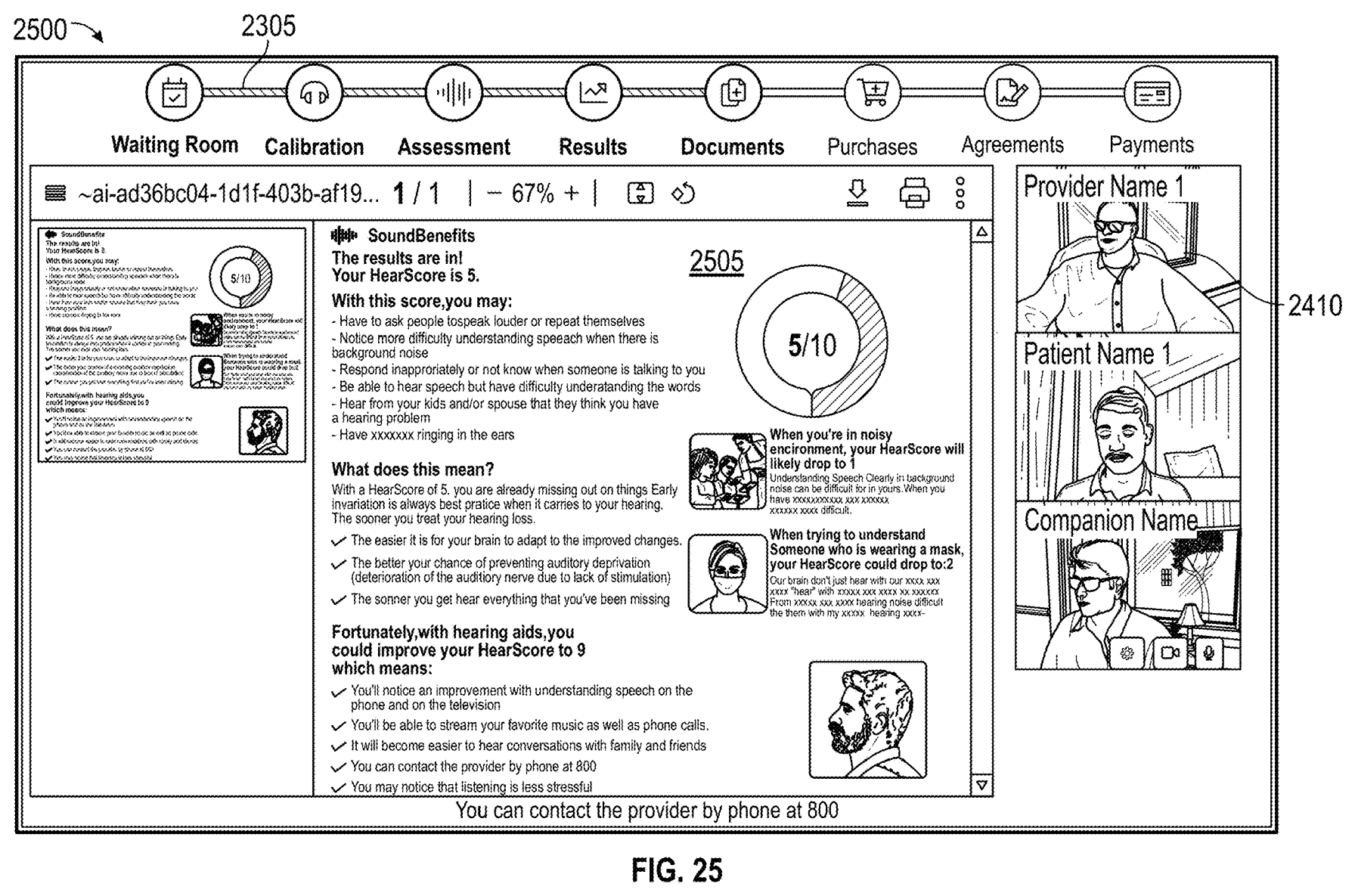
Figure 26:
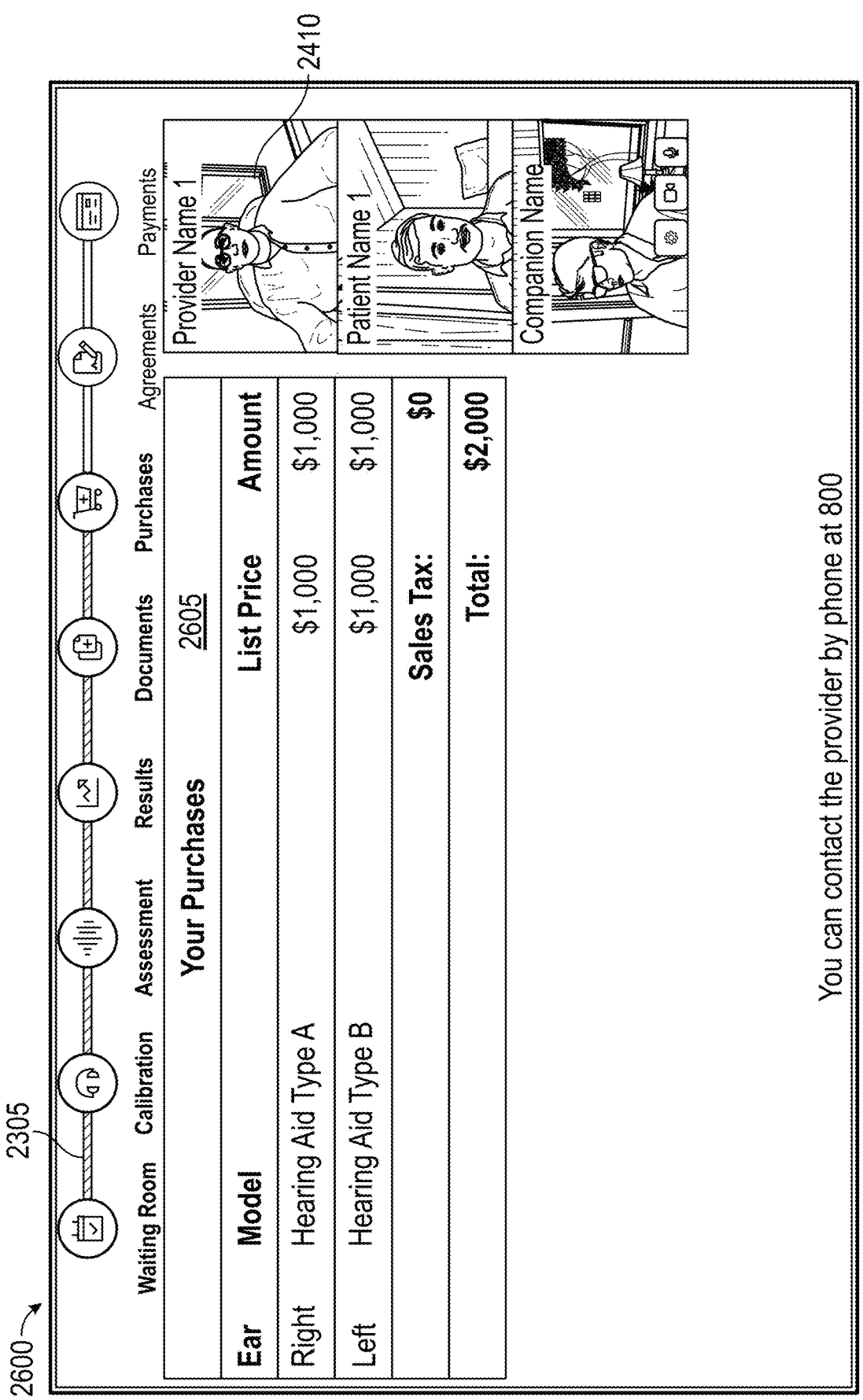
FIG. 26 is an example GUI for displaying purchase information on a guest device, in embodiments.

FIG. 23 is an example GUI 2300 for a waiting room for a guest device, in embodiments. The GUI 2300 may include a status 2305 that is similar to that displayed to a patient. The guest may also be able to see video of a provider 2310, a patient 2315, and the guest 2320 while in the waiting room. In various embodiments, other portions of the assessment related to different positions of the status 2305 may cause displays similar to that seen by the patient to be displayed on the guest device GUI. For example, FIG. 24 is an example GUI 2400 for displaying hearing test results and documentation to a guest on a guest device, in embodiments. Video chat 2410 continues to show video of the provider, patient, and guest. FIG. 25 is an example GUI 2500 for displaying documentation 2505 on a guest device, in embodiments. The documentation 2505 may be the same as selected by the provider and viewed by the patient as described herein. FIG. 26 is an example GUI 2600 for displaying purchase information 2605 on a guest device, in embodiments. In various embodiments, the guest may be able to view purchase information as a patient makes a purchase, or the guest themselves may be shown information on their device for facilitating a purchase (e.g., so that the guest may pay for any devices or services).

Figure 27:
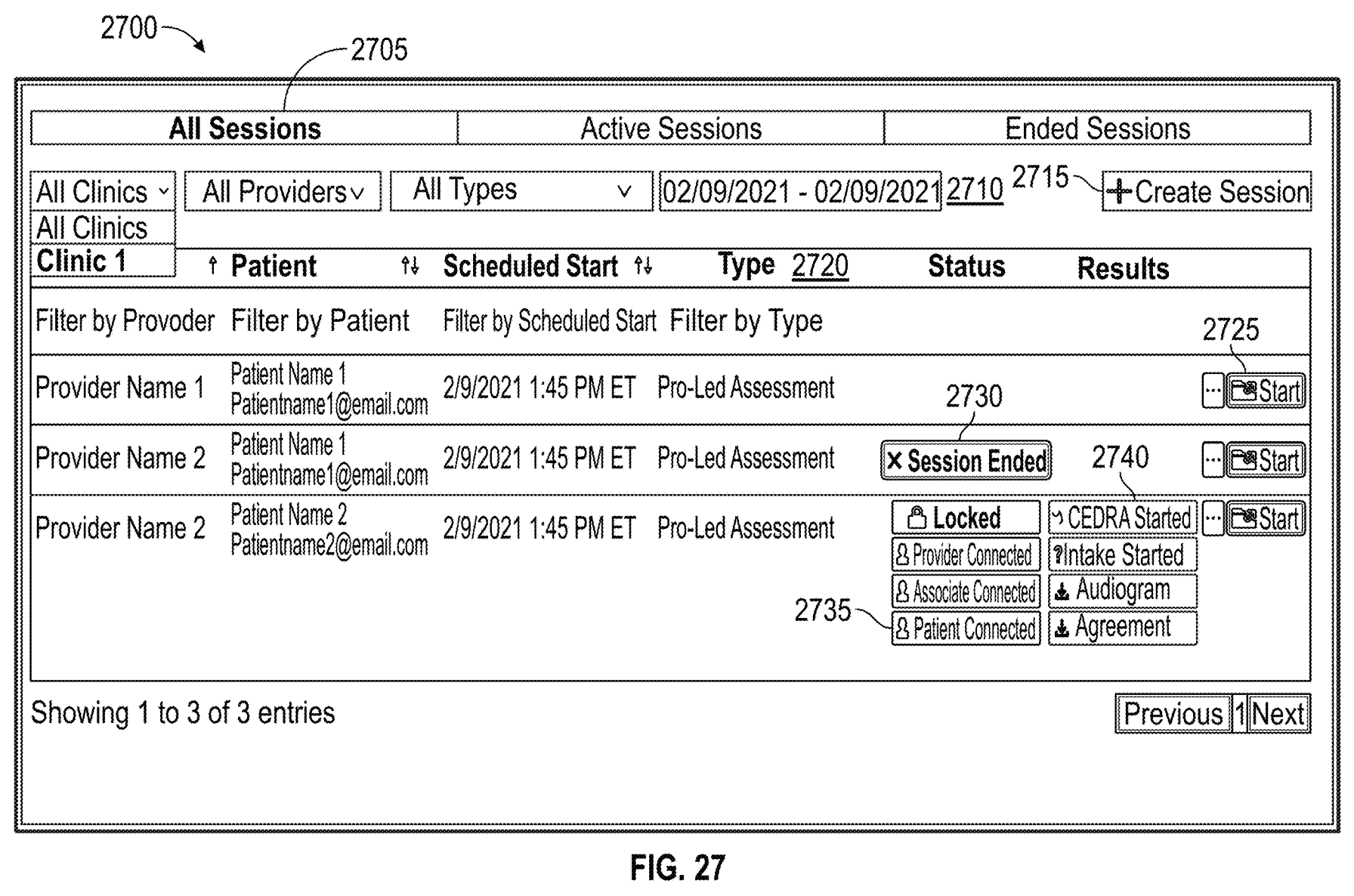

FIG. 27 is an example GUI 2700 for managing hearing test appointments on a provider device, in embodiments. The GUI 2700 may be used to manage different hearing assessments. For example, the GUI 2700 may be used additionally or alternatively to the GUI 300 in FIG. 3. The GUI 2700 includes a session type selector 2705, which allows a provider to view all relevant sessions for that provider, active sessions, or ended sessions. The sessions viewed may also be filtered or sorted using a dialog 2710, which may sort for sessions by date, type, specific provider, or clinic. A button 2715 may be selected to create a new session (e.g., if a patient has called to schedule a new session as opposed to scheduling online such that a new session is automatically populated in the GUI 2700).

The GUI 2700 further includes information about the sessions in dialog 2720. The dialog 2720 may include a button 2725 to start a session. Status information in the dialog 2720 may include information 2730 that a session has been ended. Information 2735 may indicate a status of an active session. In the example of FIG. 27, the information 2735 indicates that the session is locked (e.g., no one new may join, or no one new may join without a token generated or other authorization by the provider), that the provider is connected and in the session, that an associate is connected and in the session, and that a patient is connected and in the session. In some embodiments, the information 2735 could also indicate whether a guest is connected and in the session, and whether any of the provider, guest, patient, and/or associate are not in the session. Results information 2740 may be selectable to aspect various information about a session, such as a CEDRA form, an intake questionnaire, the audiogram generated during the session, and any agreements signed by the patient during the session. In this way, a provider may easily manage their sessions, and see which sessions are active, completed, upcoming, etc.

The information recorded in the audiogram and/or the activity log may be stored by a server in a database, for example. Such information may be later referred to for various purposes. For example, if the patient's hearing is checked at a later date, their results can be compared to historical results of other hearing tests. The activity log data may also be used for quality control to ensure that hearing tests are properly administered. The information logged by the activity log may also include any click or interaction with the GUIs of the systems and methods described herein that is performed by either of the patient or the provider.

The server and database may also store audio clips associated with different levels and types of hearing loss. These audio clips may simulate adjusted audio for a particular hearing loss (e.g., mark of an audiogram) to play for the patient. The audio clips may simulate a sound (e.g., the sound of rain) but adjusted for the patient's particular hearing loss. In this way, the patient may be able to hear a clip of what that sound may sound like if they had a well calibrated hearing aid using the results of the hearing test.

In various embodiments, the provider may vary the sequence of a test (or an automated sequence of sounds may be randomized) to prevent fraud by a patient and/or provider when taking a hearing test. In other words, by skipping around the audiogram to different locations and playing sounds, the patient would not be able to anticipate when they should and should not hear sounds. In addition, the sounds generated may be played in an automated, yet random order, so that a provider cannot assist in generated a fraudulent audiogram. The information in the activity log may further indicate whether a test was inaccurate. For example, provider played (or an automatic sequence of sounds) may be played to a patient that include the same sounds at different times mixed in to the sequence. That way, an indicator of an inaccurate test may be determined if a patient hears a sound one time and does not indicate hearing the same sound when the sound is played again later during the same test.

The systems and method described herein may further be used to implement any type of hearing tests, including for example speech recognition threshold (SRT) tests, word recognition testing to generate word recognition scores (WRS). For example, audio clips of known words may be played for the patient. The words may be shown as different buttons to the provider, and the patient may say or type the words they hear so the provider can determine accuracy. The provider may also indicate for each word audio file played whether the patient correctly identified the word. If the patient inputs the word they hear (e.g., through typing), the accuracy and results for each word clip may be automatically determined and recorded by the system.

As discussed above with respect to FIG. 19, a provider may also be able to screen capture the video captured by a camera of the patient device. For example, some methods of making a customized hearing aid include measuring a distance for a wire of a custom hearing aid. To do this remotely, a provider and/or the GUIs described herein may instruct a patient to hold a reference object (e.g., a coin) near their ear. The provider may then initiate a screen capture of an image while the patient holds the coin near their ear, and that picture may be used to estimate a required wire length for a hearing aid for the patient because the coin provides a known dimension for scaling the image and measuring an approximate measurement of the patient's ear size for sizing a wire.

In various embodiments, a patient may also be navigated through a web application to different providers, employees of a provider, etc., before or after the appointment. For example, a patient may be switched to a session with a sales person or financing person to facilitate sale of a hearing aid after the hearing test, or may be in a session with a virtual receptionist before an appointment with a provider.

Figure 28:
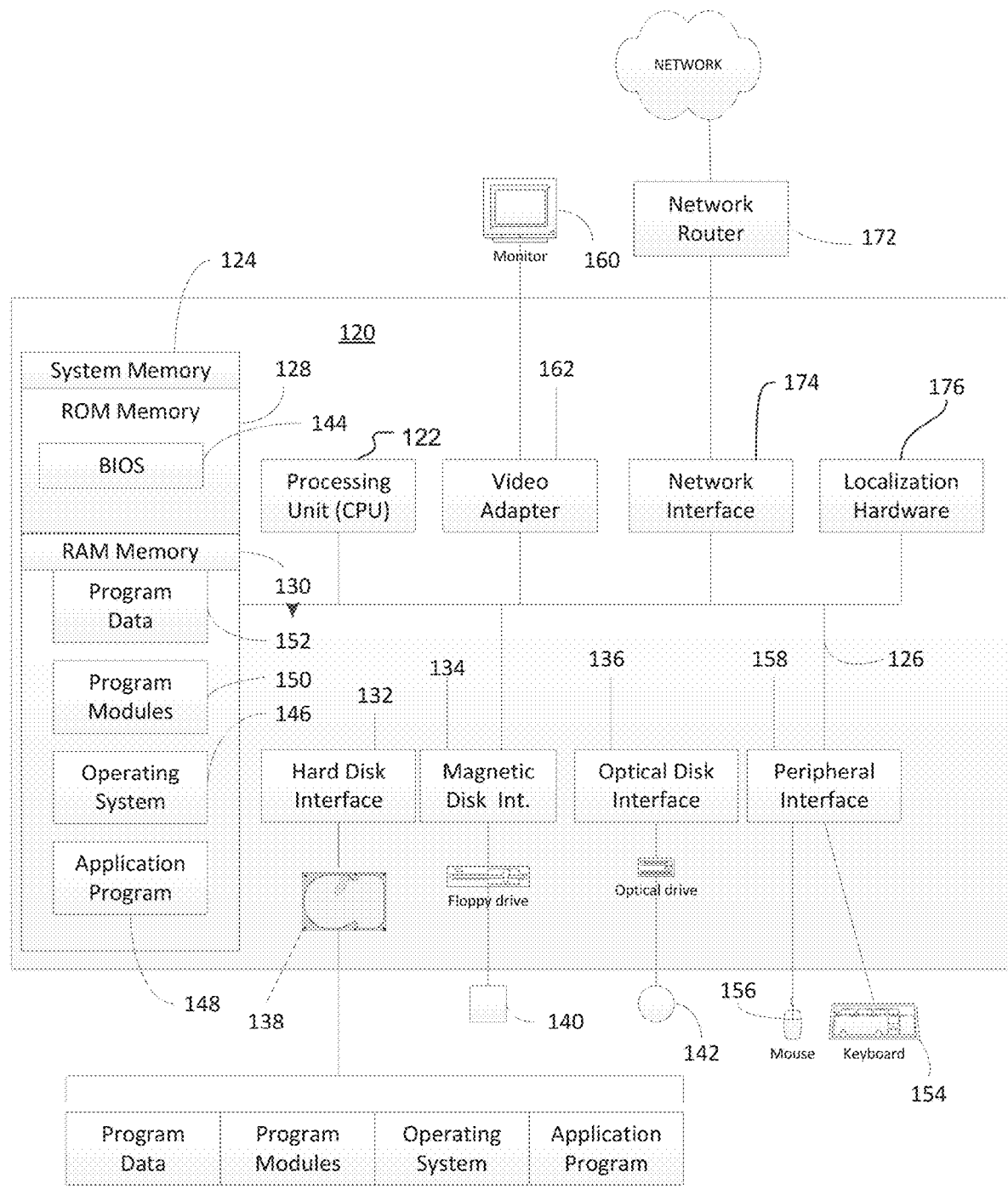
FIG. 28 is a diagrammatic view of an example user computing environment, according to some embodiments.

FIG. 28 is a diagrammatic view of an illustrative computing system that includes a general purpose computing system environment 120, such as a desktop computer, laptop, smartphone, tablet, or any other such device having the ability to execute instructions, such as those stored within a non-transient, computer-readable medium. Furthermore, while described and illustrated in the context of a single computing system 120, those skilled in the art will also appreciate that the various tasks described hereinafter may be practiced in a distributed environment having multiple computing systems 120 linked via a local or wide-area network in which the executable instructions may be associated with and/or executed by one or more of multiple computing systems 120.

In its most basic configuration, computing system environment 120 typically includes at least one processing unit 122 and at least one memory 124, which may be linked via a bus 126. Depending on the exact configuration and type of computing system environment, memory 124 may be volatile (such as RAM 130), non-volatile (such as ROM 128, flash memory, etc.) or some combination of the two. Computing system environment 120 may have additional features and/or functionality. For example, computing system environment 120 may also include additional storage (removable and/or non-removable) including, but not limited to, magnetic or optical disks, tape drives and/or flash drives. Such additional memory devices may be made accessible to the computing system environment 120 by means of, for example, a hard disk drive interface 132, a magnetic disk drive interface 134, and/or an optical disk drive interface 136. As will be understood, these devices, which would be linked to the system bus 126, respectively, allow for reading from and writing to a hard disk 138, reading from or writing to a removable magnetic disk 140, and/or for reading from or writing to a removable optical disk 142, such as a CD/DVD ROM or other optical media. The drive interfaces and their associated computer-readable media allow for the nonvolatile storage of computer readable instructions, data structures, program modules and other data for the computing system environment 120. Those skilled in the art will further appreciate that other types of computer readable media that can store data may be used for this same purpose. Examples of such media devices include, but are not limited to, magnetic cassettes, flash memory cards, digital videodisks, Bernoulli cartridges, random access memories, nanodrives, memory sticks, other read/write and/or read-only memories and/or any other method or technology for storage of information such as computer readable instructions, data structures, program modules or other data. Any such computer storage media may be part of computing system environment 120.

A number of program modules may be stored in one or more of the memory/media devices. For example, a basic input/output system (BIOS) 144, containing the basic routines that help to transfer information between elements within the computing system environment 120, such as during start-up, may be stored in ROM 128. Similarly, RAM 130, hard drive 138, and/or peripheral memory devices may be used to store computer executable instructions comprising an operating system 146, one or more applications programs 148 (such as a Web browser, retailer's mobile app, retailer's point-of-sale checkout and ordering program, and/or other applications that execute the methods and processes of this disclosure), other program modules 150, and/or program data 152. Still further, computer-executable instructions may be downloaded to the computing environment 120 as needed, for example, via a network connection.

An end-user, e.g., a customer, retail associate, and the like, may enter commands and information into the computing system environment 120 through input devices such as a keyboard 154 and/or a pointing device 156. While not illustrated, other input devices may include a microphone, a joystick, a game pad, a scanner, etc. These and other input devices would typically be connected to the processing unit 122 by means of a peripheral interface 158 which, in turn, would be coupled to bus 126. Input devices may be directly or indirectly connected to processor 122 via interfaces such as, for example, a parallel port, game port, firewire, or a universal serial bus (USB). To view information from the computing system environment 120, a monitor 160 or other type of display device may also be connected to bus 26 via an interface, such as via video adapter 162. In addition to the monitor 160, the computing system environment 120 may also include other peripheral output devices, not shown, such as speakers and printers.

The computing system environment 120 may also utilize logical connections to one or more computing system environments. Communications between the computing system environment 120 and the remote computing system environment may be exchanged via a further processing device, such a network router 172, that is responsible for network routing. Communications with the network router 172 may be performed via a network interface component 174. Thus, within such a networked environment, e.g., the Internet, World Wide Web, LAN, or other like type of wired or wireless network, it will be appreciated that program modules depicted relative to the computing system environment 120, or portions thereof, may be stored in the memory storage device(s) of the computing system environment 120.

The computing system environment 120 may also include localization hardware 176 for determining a location of the computing system environment 120. In embodiments, the localization hardware 176 may include, for example only, a GPS antenna, an RFID chip or reader, a WiFi antenna, or other computing hardware that may be used to capture or transmit signals that may be used to determine the location of the computing system environment 120.

While this disclosure has described certain embodiments, it will be understood that the claims are not intended to be limited to these embodiments except as explicitly recited in the claims. On the contrary, the instant disclosure is intended to cover alternatives, modifications and equivalents, which may be included within the spirit and scope of the disclosure. Furthermore, in the detailed description of the present disclosure, numerous specific details are set forth in order to provide a thorough understanding of the disclosed embodiments. However, it will be obvious to one of ordinary skill in the art that systems and methods consistent with this disclosure may be practiced without these specific details. In other instances, well known methods, procedures, components, and circuits have not been described in detail as not to unnecessarily obscure various aspects of the present disclosure.

Some portions of the detailed descriptions of this disclosure have been presented in terms of procedures, logic blocks, processing, and other symbolic representations of operations on data bits within a computer or digital system memory. These descriptions and representations are the means used by those skilled in the data processing arts to most effectively convey the substance of their work to others skilled in the art. A procedure, logic block, process, etc., is herein, and generally, conceived to be a self-consistent sequence of steps or instructions leading to a desired result. The steps are those requiring physical manipulations of physical quantities. Usually, though not necessarily, these physical manipulations take the form of electrical or magnetic data capable of being stored, transferred, combined, compared, and otherwise manipulated in a computer system or similar electronic computing device. For reasons of convenience, and with reference to common usage, such data is referred to as bits, values, elements, symbols, characters, terms, numbers, or the like, with reference to various embodiments of the present invention.

It should be borne in mind, however, that these terms are to be interpreted as referencing physical manipulations and quantities and are merely convenient labels that should be interpreted further in view of terms commonly used in the art. Unless specifically stated otherwise, as apparent from the discussion herein, it is understood that throughout discussions of the present embodiment, discussions utilizing terms such as "determining" or "outputting" or "transmitting" or "recording" or "locating" or "storing" or "displaying" or "receiving" or "recognizing" or "utilizing" or "generating" or "providing" or "accessing" or "checking" or "notifying" or "delivering" or the like, refer to the action and processes of a computer system, or similar electronic computing device, that manipulates and transforms data. The data is represented as physical (electronic) quantities within the computer system's registers and memories and is transformed into other data similarly represented as physical quantities within the computer system memories or registers, or other such information storage, transmission, or display devices as described herein or otherwise understood to one of ordinary skill in the art.

What is claimed is:

1. A method comprising:
receiving, by a processor of a patient electronic device, first data indicative of a graphical user interface for calibrating audio for a hearing test implemented by the patient electronic device and a provider electronic device;
display, by the processor, the graphical user interface on a display of the patient electronic device, wherein the graphical user interface comprises:
an indicator configured to indicate that a reference audio signal is being output to a speaker of the patient electronic device, and
a video chat element configured to display video of a provider captured by a camera in communication with the provider electronic device;
receiving, by the processor, second data indicative of an instruction to play the reference audio signal on the speaker of the patient electronic device, wherein the second data is sent to the patient electronic device based on a user input at the provider electronic device; and output, by the processor the reference audio signal to the speaker while causing the indicator to visually indicate that the reference audio signal is being output to the speaker of the patient electronic device.

2. The method of claim 1, further comprising receiving, by the processor after the reference audio signal is output to the speaker, third data indicative of a user adjustment to volume of the speaker.

3. The method of claim 1, wherein the patient electronic device and the provider electronic device are physically remote from one another.

4. The method of claim 1, wherein the second data further comprises an instruction to play the reference audio signal on the speaker of the patient electronic device through only one of a left speaker of the patient electronic device or a right speaker of the patient electronic device.

5. The method of claim 1, wherein the instruction is a first instruction, and wherein the method further comprises:
receiving, by the processor, third data indicative of a second instruction to stop playing the reference audio signal on the speaker of the patient electronic device; and
cause, by the processor, the reference audio signal to stop being output to the speaker.

6. The method of claim 5, further comprising causing, by the processor, the indicator to visually indicate that the reference audio signal is not being output after the reference audio signal is caused to stop being output to the speaker.

7. The method of claim 6, wherein the indicator displays at least one of:
a first color while the reference audio signal is being output to the speaker and a second color while the reference audio signal is not being output to the speaker; or
a first text while the reference audio signal is being output to the speaker and a second text while the reference audio signal is not being output to the speaker.

8. The method of claim 1, wherein the graphical user interface is a first graphical user interface, and wherein the method further comprises receiving, by the processor, third data indicative of a second graphical user interface for performing a hearing test after the audio for the hearing test is calibrated using the first graphical interface.

9. The method of claim 1, wherein the video is first video, and wherein the graphical user interface comprises a second video demonstrating to a user of the patient electronic device how to generate reference audio for comparison to the reference audio signal output to the speaker.

10. The method of claim 1, wherein:
the video chat element is a first video chat element, the video is a first video, and the camera is a first camera; and
the graphical user interface comprises a second video chat element configured to display second video of a patient captured by a second camera in communication with the patient electronic device.

11. The method of claim 1, wherein:
the video chat element is a first video chat element, the video is a first video, and the camera is a first camera; and
the graphical user interface comprises a second video chat element configured to display second video of a companion captured by a second camera in communication with a companion electronic device.

12. An apparatus comprising:
an electronic display;
a memory; and
a processor operatively coupled to the memory, wherein the processor is configured to receive first non-transitory computer readable instructions for displaying a graphical user interface or execute second non-transitory computer readable instructions stored on the memory to display the graphical user interface on the electronic display, further wherein the graphical user interface comprises:
an indicator configured to indicate whether a reference audio signal for calibrating audio for a hearing test is being output to a speaker of a patient electronic device, wherein the hearing test is implemented by the patient electronic device and a provider electronic device; and
a video chat element configured to display video of a provider captured by a camera in communication with the provider electronic device;
wherein upon receipt of data from the provider electronic device, the data indicative of an instruction to play the reference audio signal on the speaker of the patient electronic device, the processor is configured to:
output the reference audio signal to the speaker of the patient electronic device, and
cause the indicator to visually indicate that the reference audio signal is being output to the speaker.

13. The apparatus of claim 12, wherein the data is first data and the instruction is a first instruction, and wherein upon receipt of second data indicative of a second instruction to stop playing the reference audio signal on the speaker of the patient electronic device, the processor is configured to:
cease the output of the reference audio signal to the speaker of the patient electronic device, and
cause the indicator to visually indicate that the reference audio signal is not being output to the speaker.

14. The apparatus of claim 12, wherein:
the video chat element is a first video chat element, the video is a first video, and the camera is a first camera; and
the graphical user interface comprises a second video chat element configured to display second video of a patient captured by a second camera in communication with the patient electronic device.

15. The apparatus of claim 12, wherein the video is first video, and wherein the graphical user interface comprises a second video demonstrating to a user of the patient electronic device how to generate reference audio for comparison to the reference audio signal output to the speaker.

16. The apparatus of claim 12, wherein the data is sent to the patient electronic device based on a user input at the provider electronic device.

17. An apparatus comprising:
a processor; and
a memory operatively coupled to the processor and having non-transitory computer readable instructions stored thereon that, upon execution by the processor, cause the apparatus to:
transmit first data indicative of a graphical user interface for display on a patient electronic device, wherein the graphical user interface comprises:
an indicator configured to indicate whether a reference audio signal for calibrating audio for a hearing test is being output to a speaker of the patient electronic device, wherein the hearing test is implemented by the patient electronic device and a provider electronic device; and a video chat element configured to display video of a provider captured by a camera in communication with the provider electronic device;

receive second data from the provider electronic device, the second data indicative of an instruction to play the reference audio signal on the speaker of the patient electronic device; and send third data indicative of the instruction to play the reference audio signal to the patient electronic device, wherein the indicator is configured to visually indicate that the reference audio signal is being output to the speaker while the patient electronic device outputs the reference audio signal to the speaker.

18. The apparatus of claim 17, wherein the instruction is a first instruction, and wherein the instructions further cause the apparatus to:

receive fourth data from the provider electronic device, the fourth data indicative of a second instruction to stop playing the reference audio signal on the speaker of the patient electronic device; and send fifth data indicative of the instruction to stop playing the reference audio signal to the patient electronic device, wherein the indicator is configured to visually indicate that the reference audio signal is not being output to the speaker while the patient electronic device is not outputting the reference audio signal to the speaker.

19. The apparatus of claim 17, wherein the instructions further cause the apparatus to:

receive patient video data from the patient electronic device; and send the patient video data to the provider electronic device.

20. The apparatus of claim 17, wherein the video is first video, and wherein the graphical user interface comprises a second video demonstrating to a user of the patient electronic device how to generate reference audio for comparison to the reference audio signal output to the speaker.

21. The apparatus of claim 17, wherein the second data is sent to the apparatus based on a user input at the provider electronic device.

* * * * *